US009549060B2

(12) United States Patent
Wohlert et al.

(10) Patent No.: US 9,549,060 B2
(45) Date of Patent: Jan. 17, 2017

(54) METHOD AND SYSTEM FOR MANAGING MULTIMEDIA ACCESSIBLITY

(71) Applicant: AT&T Intellectual Property I, LP, Atlanta, GA (US)

(72) Inventors: Randolph Wohlert, Austin, TX (US); Aaron Bangor, Austin, TX (US); Mark Stockert, San Antonio, TX (US)

(73) Assignee: AT&T INTELLECTUAL PROPERTY I, L.P., Atlanta, GA (US)

( * ) Notice: Subject to any disclaimer, the term of this patent is extended or adjusted under 35 U.S.C. 154(b) by 212 days.

(21) Appl. No.: 14/065,866

(22) Filed: Oct. 29, 2013

(65) Prior Publication Data

US 2015/0121215 A1    Apr. 30, 2015

(51) Int. Cl.
*H04M 1/725* (2006.01)
*G06F 9/44* (2006.01)

(52) U.S. Cl.
CPC ........ *H04M 1/72591* (2013.01); *G06F 9/4446* (2013.01)

(58) Field of Classification Search
CPC ............. G06F 9/4446; H04M 1/72591; H04M 1/72588; H04M 3/42391
See application file for complete search history.

(56) References Cited

U.S. PATENT DOCUMENTS

| | | |
|---|---|---|
| 5,146,502 A | 9/1992 | Davis |
| 5,539,806 A | 7/1996 | Allen et al. |
| 5,737,389 A | 4/1998 | Allen |
| 5,809,112 A | 9/1998 | Ryan |
| 5,956,668 A | 9/1999 | Alshawi et al. |
| 5,982,853 A | 11/1999 | Liebermann |
| 6,061,431 A | 5/2000 | Knappe et al. |
| 6,212,496 B1 | 4/2001 | Campbell et al. |
| 6,477,239 B1 * | 11/2002 | Ohki .................... G09B 21/009 348/14.01 |

(Continued)

FOREIGN PATENT DOCUMENTS

JP    2004248022 A    9/2004

OTHER PUBLICATIONS

Charlton, N. et al., "User requirements for the session initiation protocol (SIP) in support of deaf, hard of hearing and speech-impaired individuals", http://tools.ietf.org/html/rfc3351, 2002.

*Primary Examiner* — Amy Ng
*Assistant Examiner* — Tan Tran
(74) *Attorney, Agent, or Firm* — Guntin & Gust, PLC; Atanu Das

(57) ABSTRACT

A system that incorporates the subject disclosure may include, for example, determine a first impairment associated with a first user of a first end user device, receive user input captured at a second end user device during a communication session between the first and second end user devices, store instructions for executing a group of adjustment techniques for modifying the user input where the group of adjustment techniques includes amplifying selective frequencies and translating the user input into sign language images, select an adjustment technique from among the group of adjustment techniques, adjust the user input according to the adjustment technique to generate adjusted user input, and provide the adjusted user input to the first end user device during the communication session. Other embodiments are disclosed.

19 Claims, 14 Drawing Sheets

(56) References Cited

U.S. PATENT DOCUMENTS

| | | | |
|---|---|---|---|
| 6,546,082 B1 | 4/2003 | Alcendor et al. | |
| 6,724,862 B1* | 4/2004 | Shaffer | H04M 1/6016 |
| | | | 379/347 |
| 6,813,490 B1 | 11/2004 | Lang et al. | |
| 7,225,224 B2 | 5/2007 | Nakamura | |
| 7,277,858 B1 | 10/2007 | Weaver et al. | |
| 7,315,612 B2 | 1/2008 | McClelland | |
| 7,333,507 B2 | 2/2008 | Bravin et al. | |
| 7,529,545 B2 | 5/2009 | Rader et al. | |
| 8,280,434 B2 | 10/2012 | Garg | |
| 8,325,883 B2 | 12/2012 | Schultz et al. | |
| 8,494,507 B1* | 7/2013 | Tedesco | A61F 4/00 |
| | | | 434/112 |
| 8,566,075 B1* | 10/2013 | Bruner | H04N 21/23433 |
| | | | 704/2 |
| 2002/0112066 A1* | 8/2002 | Agraharam | H04L 12/1836 |
| | | | 709/231 |
| 2004/0081312 A1 | 4/2004 | Salpietra | |
| 2005/0042581 A1 | 2/2005 | Oh et al. | |
| 2006/0174315 A1 | 8/2006 | Kim et al. | |
| 2008/0243513 A1* | 10/2008 | Bucchieri | G09B 21/009 |
| | | | 704/270 |
| 2010/0222098 A1* | 9/2010 | Garg | H04M 1/72552 |
| | | | 455/556.1 |
| 2012/0042360 A1* | 2/2012 | Bakeir | H04L 63/101 |
| | | | 726/4 |
| 2013/0079061 A1 | 3/2013 | Jadhav et al. | |

\* cited by examiner

100

200

400

800

1000

1100

US 9,549,060 B2

METHOD AND SYSTEM FOR MANAGING MULTIMEDIA ACCESSIBLITY

FIELD OF THE DISCLOSURE

The subject disclosure relates to a method and system for managing multimedia accessibility.

BACKGROUND

Communication systems are utilized for providing content to end user devices during communication sessions. The content can be of various types, such as voice, video and/or data, and can be of various formats. These formats can depend on a number of different factors including device capability and network capability. Not every one of the formats is suitable for each user, and users often have preferences as to how content is to be presented.

BRIEF DESCRIPTION OF THE DRAWINGS

Reference will now be made to the accompanying drawings, which are not necessarily drawn to scale, and wherein.

DETAILED DESCRIPTION

Figure 1:
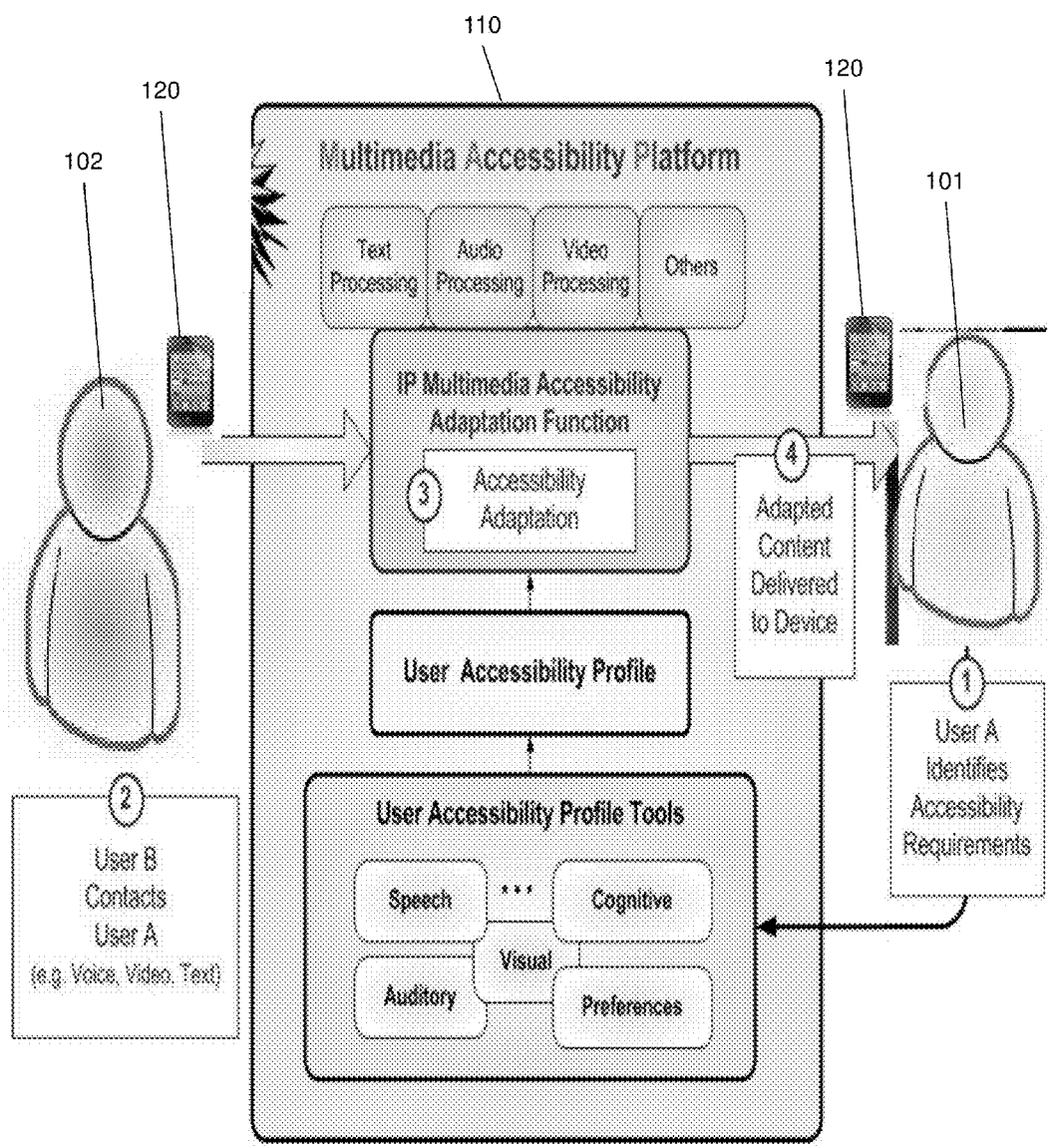
FIGS. 1-9 depict illustrative embodiments of systems for providing one or more accessibility adjustments such as during a communication session.

The subject disclosure describes, among other things, illustrative embodiments of systems and methods for providing accessibility adjustments for one or more users via adjustments to content, such as various user input including user speech, messaging, images, video and/or text, as well as other content. It should be understood that the embodiments can be utilized with all types of content. The accessibility adjustments can be based on detected or determined impairments (e.g., hearing, vision, speech, cognitive, motor skill, and so forth) and/or can be based on other factors, such as user preferences. In one or more embodiments, user preferences and accessibility requirements can be identified (e.g., in the Core Network) via accessibility profile tools. In other embodiments, media can be dynamically adapted to satisfy or address other issues, such as environmental conditions. In one or more embodiments, communications occur between users and a multimedia accessibility platform (e.g., an application server in the core network, such as an IMS core network) can adapt content to meet user's desires. The adapted content can then be provided to the end user device for presentation to the user as part of the communication session.

In one or more embodiments, adaptation functions can take into consideration network capabilities and device capabilities and/or network conditions. In one or more embodiments, an API can be provided to expose functionality to 3rd party developers. In one or more embodiments, the multimedia accessibility platform architecture can be based on a USP platform. The adaptation functionality can be provided on its own, or in an existing application server (e.g., TAS or PS). Various accessibility adjustments can be performed including selective speech frequency amplification (e.g., a hearing aid in the cloud); speech to text conversion; speech to sign language conversion; sign language to speech conversion; text adaptation (e.g., enlargement, font change, color change and so forth); text to speech conversion; closed captioning; auditory amplification in the range of music frequencies; color blindness adaptation; physical interfacing adaptation; epilepsy triggering prevention modifications (e.g., removal of selected stimuli from the content that is associated with an epilepsy trigger); input/output device capability enhancements; core network intelligence considerations. In one or more embodiments, multiple adaptations can be performed for individuals on both the transmitting and receiving sides of a communication session or connection. For example, a user could be provided with speech amplification in addition to closed captioning.

Other embodiments are included in the subject disclosure. The exemplary embodiments can include one or more components or steps described in U.S. patent application Ser. No. 14/065,903 entitled "Method and System for Adjusting User Speech in a Communication Session" to Wohlert et al. filed contemporaneously herewith under, the disclosure of which is hereby incorporated by reference herein.

One embodiment of the subject disclosure is a method that includes detecting, by a system including a processor, a communication session between a first end user device and a second end user device. The system can store instructions for executing a group of adjustment techniques for modifying user input, where the group of adjustment techniques includes amplifying selective frequencies for a first degree of impairment and translating the user input into sign language images for a second degree of impairment, and where the second degree of impairment is more severe than the first degree of impairment. The method can include determining, by the system, a first impairment associated with a first user of the first end user device. The system can determine a degree of impairment for the first impairment and can receive the user input captured at the second end user device during the communication session. The system can select an adjustment technique from among the group of adjustment techniques according to the degree of impairment for the first impairment and can access an impairment profile for the first user. The system can adjust the user input according to the adjustment technique and the impairment profile to generate adjusted user input. The system can provide the adjusted user input to the first end user device during the communication session.

One embodiment of the subject disclosure includes system having a memory to store executable instructions and a processor coupled with the memory. The processor, responsive to executing the executable instructions, can perform operations including storing instructions for executing a group of adjustment techniques for modifying user input, where the group of adjustment techniques includes amplifying selective frequencies and translating the user input into sign language images. The processor can determine a first impairment associated with a first user of a first end user device and can receive user input captured at a second end user device during a communication session between the first and second end user devices. The processor can select an adjustment technique from among the group of adjustment techniques and can adjust the user input according to the adjustment technique to generate adjusted user input. The processor can provide the adjusted user input to the first end user device during the communication session.

One embodiment of the subject disclosure includes a computer-readable storage device comprising computer instructions which, responsive to being executed by a processor of a first end user device, causes the processor to perform operations including providing impairment information to a system that includes an application server. The processor can receive adjusted user input from the system during a communication session between the first end user device and a second end user device, where the adjusted user input is generated from a modification of user input captured at the second end user device during the communication session, where the modification is responsive to a detection of a first impairment of a first user of the first end user device and is based on an adjustment technique selected by the system from among a group of adjustment techniques, where instructions for executing the group of adjustment techniques is accessible to the system, and where the group of adjustment techniques includes amplifying selective frequencies and translating the user input into sign language images. The processor can present the adjusted user input at the first end user device.

FIG. 1 depicts an illustrative embodiment of a system 100 that can utilize a multimedia accessibility platform 110 (hereinafter server 110) to facilitate a communication session between a first end user 101 utilizing an end user device 120 and a second end user 102 utilizing another end user device 120. The end user devices 120 can be various types of devices including smart phones, mobile devices, laptop computers, desktop computers, landline telephones, cordless telephones, set top boxes and/or any other communication device capable of engaging in a communication session to exchange or otherwise communicate voice, video and/or data. Platform 110 is described as a server, but it should be understood that the platform 110 can be implemented using any number of computing devices (e.g., a single server in a centralized system or multiple server in a distributed environment), any type of computing devices (e.g., a service provider server or a customer computing device), and/or any configuration of the computing device(s) (e.g., a server farm where one or more servers are in a master/slave arrangement with one or more other servers or a combination of service provider devices and customer equipment performing the multimedia accessibility platform functions).

Server 110 can determine accessibility requirements or desires of one or both the users 101, 102. Server 110 can execute various processing functions (e.g., text, audio, video and so forth) to implement accessibility adaptation. The accessibility adaptation can include adjustment of the multimedia content, adjusting the presentation of the multimedia content or otherwise making adjustments associated with the presentation of the multimedia content to facilitate the accessibility by the user to the content. In one or more embodiments, adjustments to the content (e.g., text messaging, speech, images, music, graphics and so forth) can be made and provided to the end user device in a timely manner as part of the communication session so that any conversation or communication exchange is not disrupted. As an example, the server 110 can access one or more profiles associated with one or more of the first user 101, the second user 102 and/or one or both of the end user devices. These profiles can include various profile information and/or profiling tools associated with speech, auditory, visual and/or cognitive information or data for the user(s). In one or more embodiments, the server 110 can also access user preferences for one or both of the first and second users so that the preferences can be utilized in the accessibility adaptation.

Server 110 can address a number of different accessibility impairments or issues including mild hearing loss (e.g., via speech frequency amplification), severe hearing loss (e.g., via speech to text or speech to sign language graphics), speech impairment (e.g., sign language to speech or text to speech), mild vision impairment (e.g., via text adaptation), severe vision impairment (e.g., via text to speech), and/or cognitive disability (e.g., adjusting vocabulary). Server 110 can also facilitate the exchange of voice, video or data in a communications session in other ways such as by utilizing closed captioning, music frequency amplification, color blindness adaptation, physical interfacing adaptation, epilepsy triggering prevention modifications (e.g., via stimuli removal), addressing apraxia (motor planning disorder, such as speech related), language translation for cognitive disabilities (e.g. based on educational level, dyslexia, cerebral palsy, epilepsy, and so forth), and/or smart adaptation (e.g., device limitations, presentation environment, and so forth).

In one or more embodiments, the server 110 can determine a first impairment associated with first user 101 of first end user device 120, and can receive user input captured at second end user device 120 during a communication session between the first and second end user devices. The server 110 can store instructions for executing a group of adjustment techniques for modifying the user input, where the group of adjustment techniques includes amplifying selective frequencies and translating the user input into sign language images. The server 110 can select an adjustment technique from among the group of adjustment techniques. The server 110 can adjust the user input according to the adjustment technique to generate adjusted user input. The server 110 can provide the adjusted user input to the first end user device 120 during the communication session.

In one or more embodiments, the server 110 can determine a degree of impairment for the first impairment, where the selecting of the adjustment technique from among the group of adjustment techniques is according to the degree of impairment for the first impairment. The server 110 can access an impairment profile for the first user 101, where the adjusting of the user input to generate the adjusted user input is according to the impairment profile. The amplifying of selective frequencies can be utilized for a first degree of impairment. The translating of the user input into sign language images can be utilized for a second degree of impairment, where the second degree of impairment is more severe than the first degree of impairment.

In one or more embodiments, the server 110 can include or otherwise be in communication with an application programming interface accessible by a remote device that is operated by a third party that is different from a service provider operating the server, where at least a portion of the instructions for executing the group of adjustment techniques are received from the remote device.

In one or more embodiments, the server 110 can be an application server of an IP multimedia subsystem network that facilitates combined services of circuit-switched and packet-switched systems, and can be in communication with a serving call session control function and a media resource function of the IP multimedia subsystem network.

In one or more embodiments, the server 110 can determine a second impairment associated with the second user 102 of the second end user device 120 and can receive other user input captured at the first end user device during the communication session. The server 110 can select another adjustment technique from among the group of adjustment techniques and can adjust the other user input according to the adjustment technique to generate adjusted other user input. The server 110 can provide the adjusted other user input to the second end user device during the communication session.

In one or more embodiments, the server 110 can access an impairment profile for the first user 101, where the adjusting of the user input to generate the adjusted user input is according to the impairment profile, where the impairment profile includes vision information for the first user, and where the group of adjustment techniques includes modifying graphics generated at the second end user device according to the vision information. The server 110 can obtain the vision information for the first user 101 by one of a vision test at a communication device (which can be the first end user device 120 or another device) of the first user prior to the communication session or receiving the vision information from a remote source operated by a third party that is different from a service provider operating the system.

Figure 2:
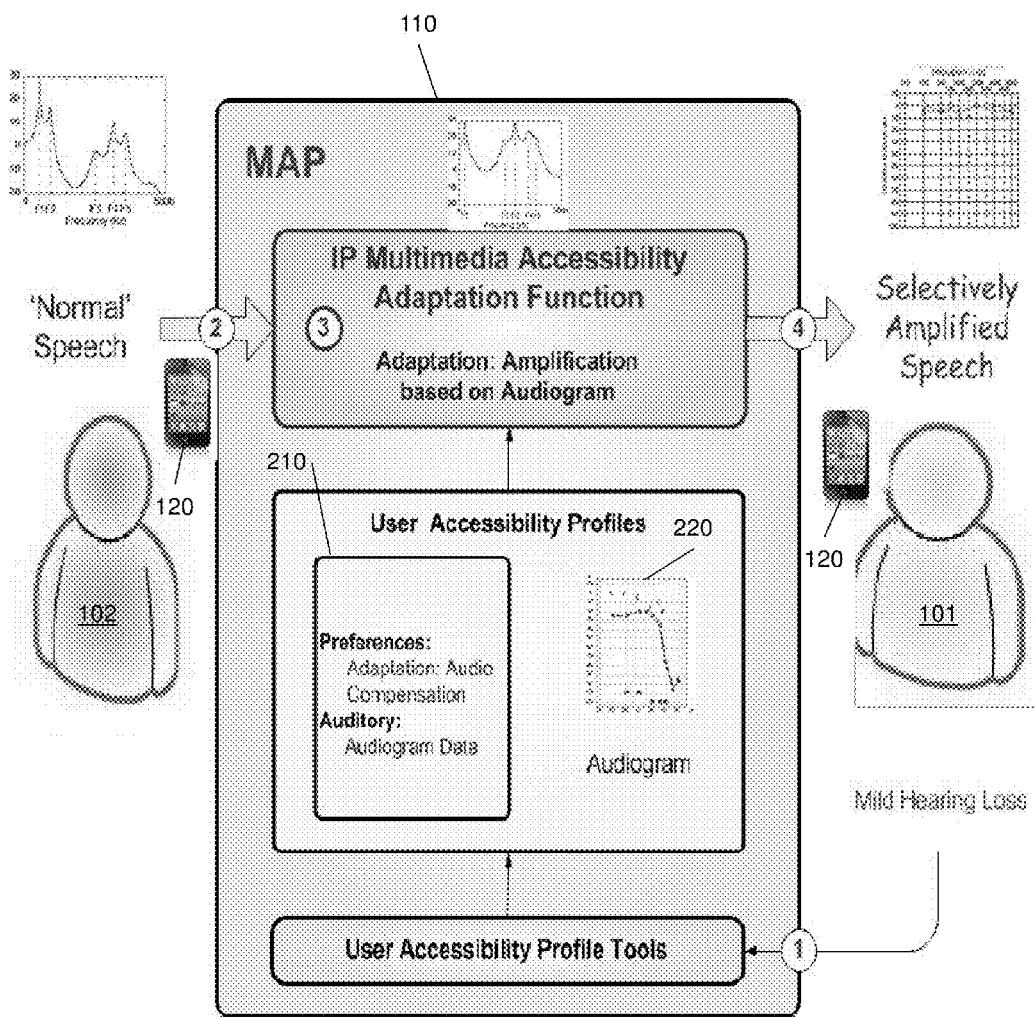

FIG. 2 depicts an illustrative embodiment of system 200 in which a hearing impairment, such as mild hearing loss, is detected and addressed via accessibility adjustment. In one embodiment, the server 110 can determine that the user 101 has a mild hearing loss such as via accessing information included in profile 210. The profile 210 can be various types of profiles such as a user profile that includes user preferences, user impairments (e.g., in an impairment sub-profile for the user 101), subscriber data, QoS data and so forth. In one embodiment, the profile 210 can include audio diagnostic data for the user 101, such as an audiogram 220 that provides data to indicate the user's ability to hear, such as based on different frequencies, different intensity and so forth.

In one embodiment, the audiogram can be indicative of the user's hearing thresholds which are discovered by using behavioral hearing tests or physiological tests, such as via audiometry. In one embodiment, the hearing test can be provided at the end user device 120 or at another communication device of the user, can include different tones being presented at a specific frequency (pitch) and intensity (loudness), and the user 101 can provide user input to indicate that he or she has heard the sound. The lowest intensity sound that is heard can be recorded. In another embodiment, the audiogram can be obtained from a remote source, such as a medical provider of the user 101 or some other entity that is unaffiliated with the service provider operating the server 110.

In system 200, the server 110 can utilize the audiogram data to selectively amplify portions of speech of user 102 during the communication session. The server 110 can provide the adjusted user speech to the end user device 120 of user 101 for presentation. The timeliness of the amplification and the providing of the adjusted content can enable the communication session to continue uninterrupted. As an example, certain frequencies identified in the audiogram as being frequencies that are difficult for the user 101 to hear, can be amplified by the server 110 and can be provided to the end user device 120 of the user 101 to be presented as adjusted speech content. In one or more embodiments, the implementation of selective frequency amplification as an adjustment technique can be based on user preferences, such as indicated in the profile 210, although in other embodiments the use of selective frequency amplification can be initiated based on other factors, such as user input at the beginning of a communication session.

In one or more embodiments, the server 110 can store (locally and/or remotely) instructions for executing a group of adjustment techniques for modifying user input (e.g., user speech). The group of adjustment techniques can include amplifying selective frequencies, as well as other adjustment techniques such as translating the user input into sign language images. In one embodiment, the selection of the particular technique among the group can be based on user preferences. In another embodiment, the selection of the technique from among the group of techniques can be based on a degree of user impairment. For example, the use of selective frequency amplification can be for a first degree of impairment and the translation into sign language images can be for a second degree of impairment, where the second degree of impairment is more severe than the first degree of impairment.

Figure 3:
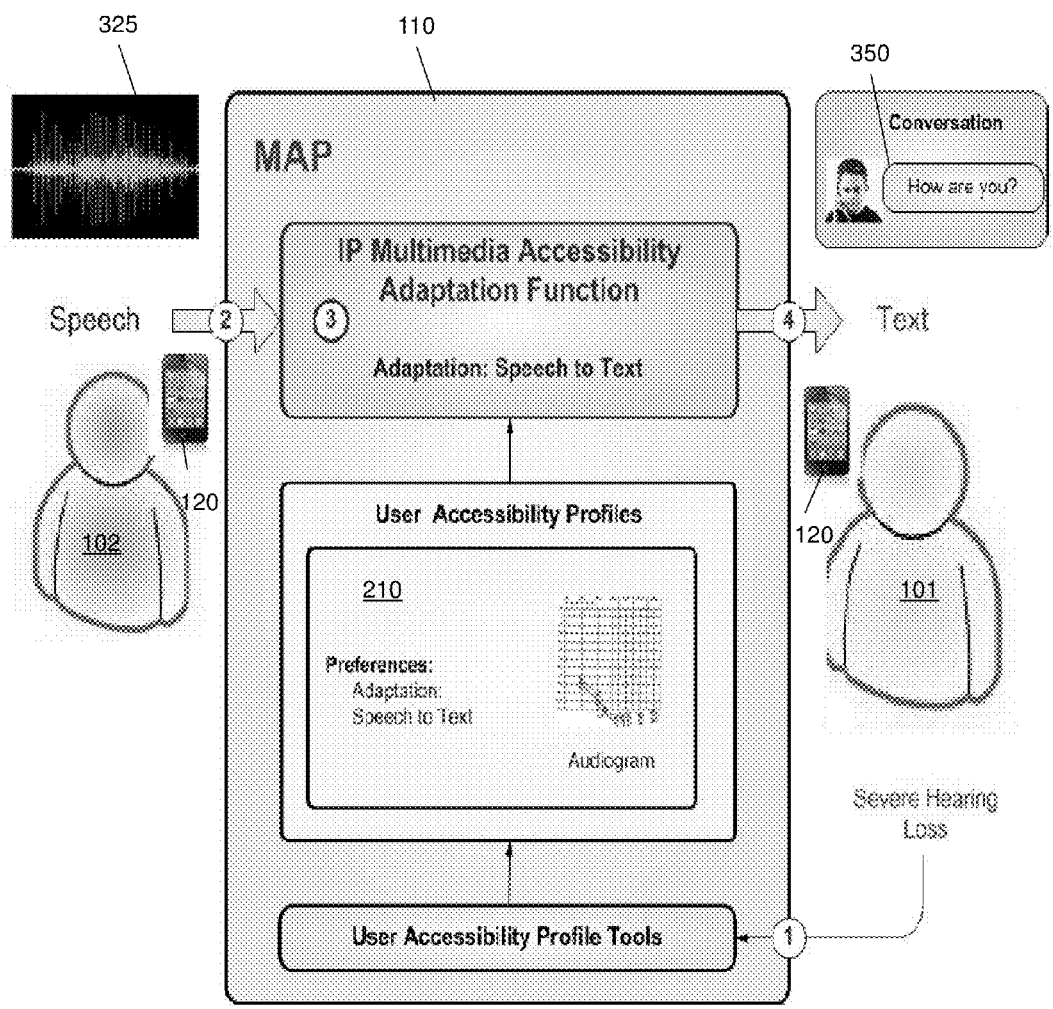

FIG. 3 depicts an illustrative embodiment of system 300 in which a hearing impairment, such as a severe hearing loss, is detected and addressed via accessibility adjustment. In one embodiment, the server 110 can determine that the user 101 has a severe hearing loss such as via accessing information included in the profile 210. In another embodiment, server 110 can determine that the user 101 has a preference for speech-to-text conversion such as via preferences identified in the profile 210. In this embodiment, the server 110 can receive user speech 325 captured at end user device 120 of second user 102. The server 110 can apply speech recognition to the user speech 325 to generate text 350 representative of the user speech which is then provided to end user device 120 of user 101 for presentation.

Various libraries can be utilized as part of the speech recognition process, including natural language libraries. In one or more embodiments, the libraries utilized for the speech recognition can be selected based on an identification of one or both of user 101, 102. For instance, user 102 can be identified as speaking with a particular accent and a library corresponding to that accent can be utilized. Other information, such as age, educational background, nationality, geographic location and so forth of one or both of the users 101, 102 can be used as criteria in selecting libraries for generating the text 350 via speech recognition. In one embodiment, the user can have his or her own library that is customized and adjusted over time.

In one or more embodiments, both the text 350 and the original audio-version of the user speech 325 can be provided to the end user device 120 of first user 101 for presentation. In another embodiment, the user speech 325 can be adjusted, such as selective frequency amplification, and can be provided to the end user device 120 of first user 101, along with the text 350.

In one embodiment, the text 350 can be provided for all of the user speech 325 or just a portion of the user speech. For instance, the server 110 can identify a phrase that include frequencies that are difficult for the user 101 to hear (e.g., via an audiogram for the user) and can translate the entire phrase. In another embodiment, if a phrase does not include a difficult frequency for the user to hear then the server 110 can allow only the original user speech 325 to be provided to the end user device 120 for that phrase.

Figure 4:
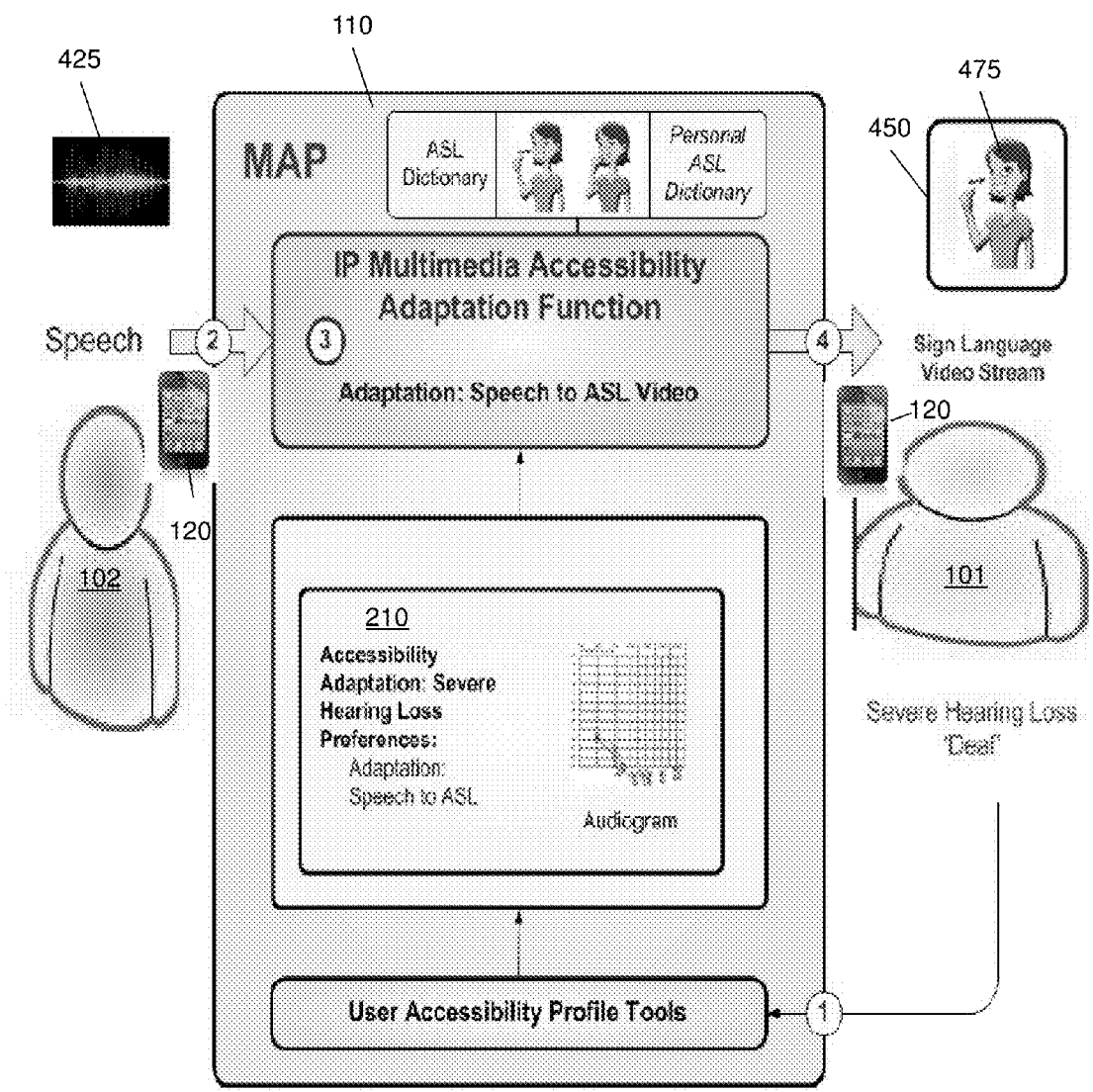

FIG. 4 depicts an illustrative embodiment of system 400 in which a hearing impairment, such as a severe hearing loss, is detected and addressed via accessibility adjustment. In one embodiment, the server 110 can determine that the user 101 has a severe hearing loss such as via accessing information included in the profile 210. In another embodiment, server 110 can determine that the user 101 has a preference for sign language images such as via preferences identified in the profile 210. In this embodiment, the server 110 can receive user speech 425 captured at end user device 120 of second user 102. The server 110 can apply speech recognition to the user speech 425 to generate or otherwise obtain sign language images 450 that are representative of the user speech and which are then provided to end user device 120 of user 101 for presentation. In one embodiment, the server 110 can first translate the user speech 425 into text, such as described in system 300, and then can translate the text into sign language images 450 (e.g., sign language images based on American Sign Language or other forms of sign language).

The generation or obtaining of the sign language images 450 can be based on various libraries or dictionaries, including libraries or dictionaries that are selected based on an identification of one or both of users 101, 102. In one embodiment, one or more of the libraries or dictionaries can be personal libraries or dictionaries of one or both of the users 101, 102, such as libraries or dictionaries that are created based on one or more of monitoring communications of the user(s), preferences of the user(s), analyzing feedback from the user(s) and so forth. Other information, such as age, educational background, nationality and so forth of one or both of the users 101, 102 can be used as criteria in selecting libraries or dictionaries for generating or obtaining the sign language images 450.

In one embodiment, the sign language images 450 can include an avatar 475 that illustrates the sign language. The avatar 475 can be a computer-generated graphical representation, such as of a person (e.g., user 102), and/or can be recorded images of a person illustrating the sign language. The avatar 475 can be customized or otherwise adjusted based on preferences of the user 101 and/or the user 102. For example, the user 101 may prefer an avatar that has an appearance similar to the appearance of user 102.

In one embodiment, the server 110 can detect a communication session between end user devices 120 of the first and second users 101, 102, and can determine an impairment associated with the first user. The server 110 can receive user speech 425 captured at the end user device 120 of the second user 102 during the communication session. Instructions for executing a group of adjustment techniques for modifying the user input 425 can be accessed by the server 110, where the group of adjustment techniques includes translating the user speech into the sign language images 450, such as based on a degree of the impairment of the first user 101. In one embodiment, different adjustment techniques can be utilized for different degrees of impairment, such as amplifying selective frequencies of the user speech 425 for a lesser degree of impairment. In this example, the server 110 can select a desired adjustment technique from among the group of adjustment techniques such as the sign language translation and can access a profile for the first user 101 (e.g., an impairment profile). The server 110 can adjust the user speech 425 according to the selected adjustment technique (e.g., sign language translation) and the impairment profile, and can provide the sign language images 450 to the end user device 120 of first user 101 during the communication session. In one embodiment, the sign language images 450 can be provided to the end user device 120 of first user 101 along with the original user speech 425. In another embodiment, the sign language images 450 can be provided to the end user device 120 of first user 101 along with a modified version of the original user speech 425, such as selected frequency amplified speech and/or text conversion. In another embodiment, the sign language images 450 can depict the avatar 475 performing sign language as well as speaking the user speech 425.

In one or more embodiments, the server 110 can modify or generate physical characteristics of the avatar 475 based on user preferences, such as included in the profile 210. In one or more embodiments, the server 110 can modify graphics based on changing size, color and/or font of text. In one or more embodiments, the server 110 can access an impairment profile of user 101 that includes vision information for the user, where the group of adjustment techniques includes modifying graphics generated at the other end user device according to the vision information, and where the server 110 obtains the vision information for the user 101 by one of a vision test at a communication device of the user 101 prior to the communication session or receiving the vision information from a remote source operated by a third party that is different from a service provider operating the system.

Figure 5:
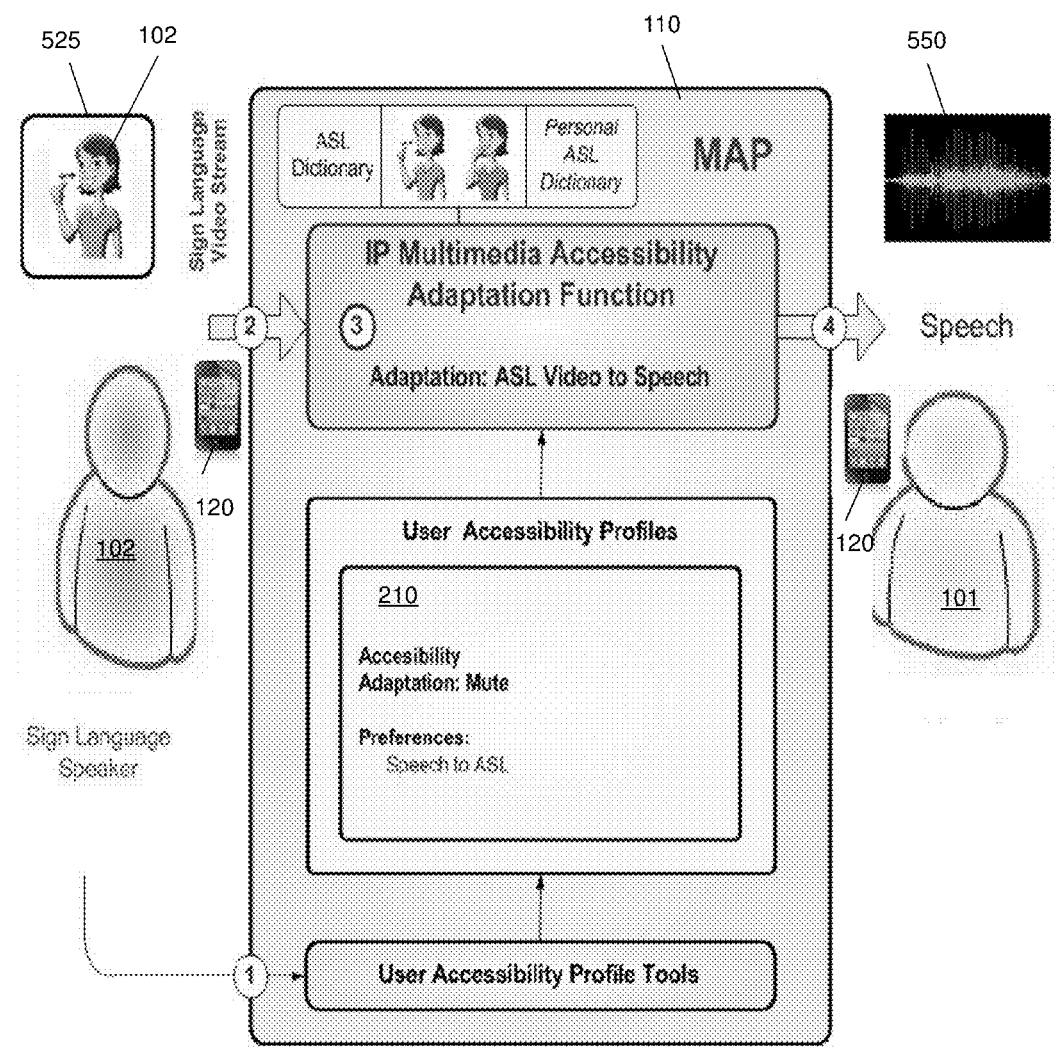

FIG. 5 depicts an illustrative embodiment of system 500 in which a speech impairment is detected and addressed via accessibility adjustment. In one embodiment, the server 110 can determine that the user 102 desires to communicate by sign language such as via accessing information included in the profile 210. In this embodiment, the server 110 can receive sign language images 525 captured at end user device 120 of second user 102. These sign language images can be captured by a camera or other image recording device of the end user device 120 (or in communication with the end user device). The server 110 can apply image recognition to the sign language images 525 to generate or otherwise obtain audio speech 550 that is representative of the sign language images and which is provided to end user device 120 of user 101 for presentation. In one embodiment, the server 110 can first translate the sign language images 525 into text, such as described in system 300, and then can translate the text into audio content 550.

The translation of sign language images 525 into audio speech 550 can be based on various libraries or dictionaries, including libraries or dictionaries that are selected based on an identification of one or both of users 101, 102. In one embodiment, one or more of the libraries or dictionaries can be personal libraries or dictionaries of one or both of the users 101, 102, such as libraries or dictionaries that are created based on one or more of monitoring communications of the user(s), preferences of the user(s), and so forth. Other information, such as age, educational background, nationality and so forth of one or both of the users 101, 102 can be used as criteria in selecting libraries or dictionaries for translating the sign language images 525 to the audio speech 550. In one or more embodiments, the audio speech 550 can be in various languages.

In one or more embodiments, the audio content 550 can be generated utilizing synthesized speech. In other embodiments, the audio content 550 can be generated using recorded speech. Combinations of synthesized and recorded speech can also be utilized, such as utilizing synthesized speech when a recorded version of a phrase or word is not available. The synthesized or recorded speech 550 can be adjusted based on user preferences or other factors, such as gender of voice, pitch, intensity, accent and so forth. In one or more embodiments, the audio content 550 can be provided to end user device 120 of user 101 along with the original or a modified version of the graphics (e.g., an enlarged version of a text message).

Figure 6:
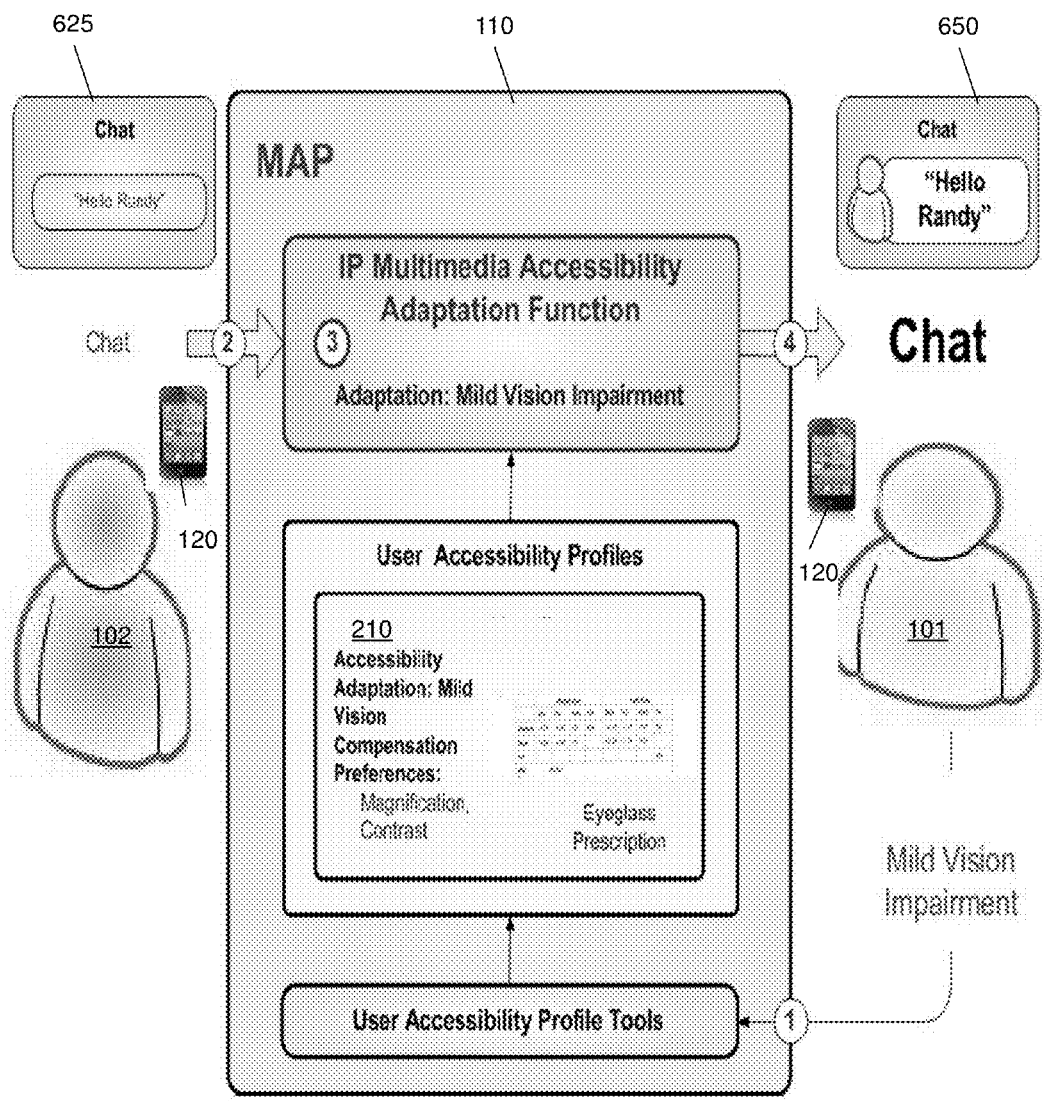

FIG. 6 depicts an illustrative embodiment of system 600 in which a vision impairment, such as a mild vision impairment, is detected and addressed via accessibility adjustment. In one embodiment, the server 110 can determine that the user 101 has a mild vision impairment such as via accessing information included in the profile 210. In another embodiment, server 110 can determine that the user 101 has a preference for particular vision-based adjustments such as via preferences identified in the profile 210. In this embodiment, the server 110 can receive graphics 625, such as SMS text message, entered at end user device 120 of second user 102. The server 110 can obtain impairment information (e.g., via an impairment profile) associated with the user 101, such as an eyeglass prescription, color blindness, dyslexia and so forth. The server 110 can modify the captured graphics based on the impairment information, such as increasing size, changing font or changing color. The modified graphics 650 can then be provided to the end user device 120 of user 101 for presentation.

In one or more embodiments, other graphics adjustments can be made to facilitate the communication session, such as adjusting the background color for the text message. In one or more embodiments, text adaptation can be performed with real time modification of HTML5 tags, CSS 3 attributes in web pages to make text larger, bolder, provide more contrast, and so forth.

Figure 7:
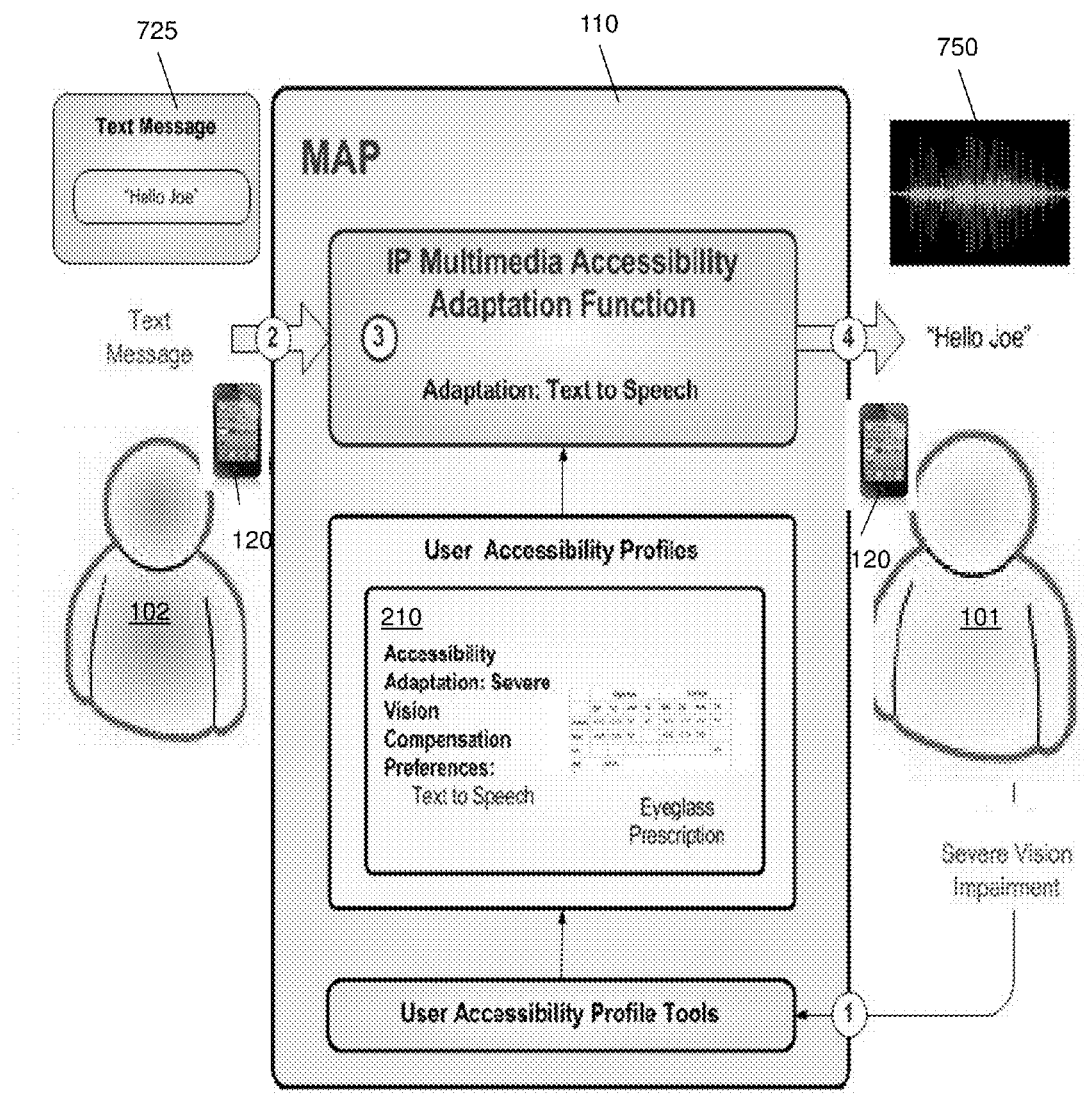

FIG. 7 depicts an illustrative embodiment of system 700 in which a vision impairment, such as a severe vision impairment, is detected and addressed via accessibility adjustment. In one embodiment, the server 110 can determine that the user 101 has a severe vision impairment such as via accessing information included in the profile 210. In another embodiment, server 110 can determine that the user 101 has a preference for particular vision-based adjustments such as via preferences identified in the profile 210. In this embodiment, the server 110 can receive graphics 725, such as SMS text message, entered at end user device 120 of second user 102. The server 110 can obtain impairment information (e.g., via an impairment profile) associated with the user 101. The server 110 can translate the captured graphics 725 based on the impairment information to generate audio content 750 representative of the captured graphics. The audio content 750 can then be provided to the end user device 120 of user 101 for presentation. In one or more embodiments, the audio content 750 can be generated based on synthesized speech. In other embodiments, the audio content 750 can be generated using recorded speech. Combinations of synthesized and recorded speech can also be utilized. The synthesized or recorded speech 725 can be adjusted based on user preferences or other factors, such as gender of voice, pitch, intensity, accent and so forth. In one or more embodiments, the audio content 750 can be provided to end user device 120 of user 101 along with the original or a modified version of the graphics 725 (e.g., an enlarged version of a text message).

Figure 8:
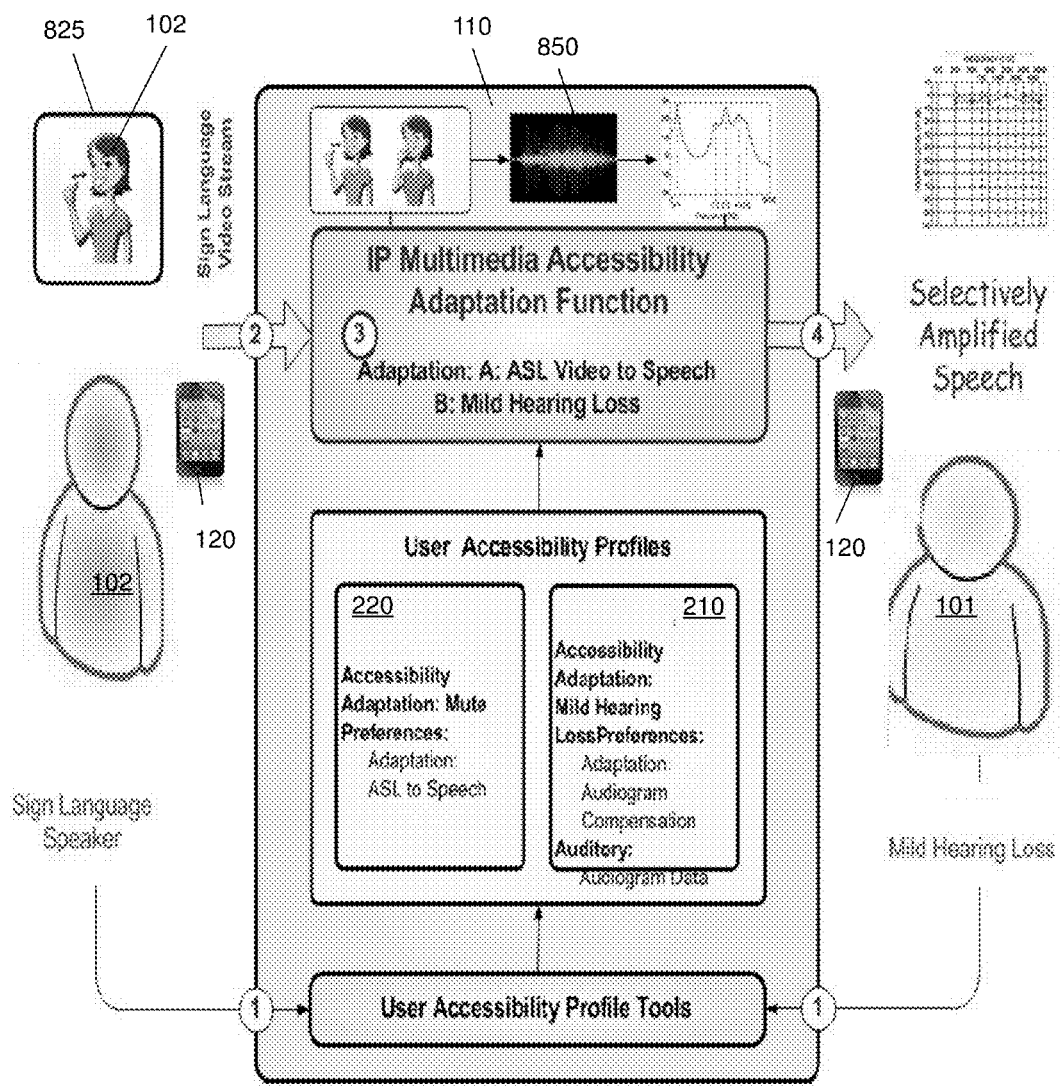

FIG. 8 depicts an illustrative embodiment of system 800 in which multiple impairments are detected or otherwise determined. For example, a speech impairment of user 102 and a hearing impairment of user 101 can be detected and addressed via accessibility adjustment. In one embodiment, the server 110 can determine that the user 102 desires to communicate by sign language such as via accessing information included in the profile 220. In one embodiment, the server 110 can determine that the user 101 desires to receive adjusted audio content such as via accessing information included in the profile 210. In this embodiment, the server 110 can receive sign language images 825 captured at end user device 120 of second user 102. The server 110 can apply image recognition to the sign language images 825 to generate or otherwise obtain audio speech 850 that is representative of the sign language images. The audio speech 850 can be modified by server 110 based on impairment information from the profile 210, such as an audiogram for the user 101. For example, selected frequencies identified in the audiogram can be amplified in the audio speech to generate an adjusted audio speech which is provided to end user device 120 of user 101 for presentation. In one embodiment, the server 110 can first translate the sign language images 825 into text, such as described in system 300, and then can translate the text into audio content 850 which is then further modified based on the hearing impairment of user 101.

The translation of the sign language images 825 can be based on various libraries or dictionaries, including libraries or dictionaries that are selected based on an identification of one or both of users 101, 102. In one embodiment, one or more of the libraries or dictionaries can be personal libraries or dictionaries of one or both of the users 101, 102, such as libraries or dictionaries that are created based on one or more of monitoring communications of the user(s), preferences of the user(s), and so forth. Other information, such as age, educational background, nationality and so forth of one or both of the users 101, 102 can be used as criteria in selecting libraries or dictionaries for translating the sign language images 825 to the audio speech 850.

Figure 9:
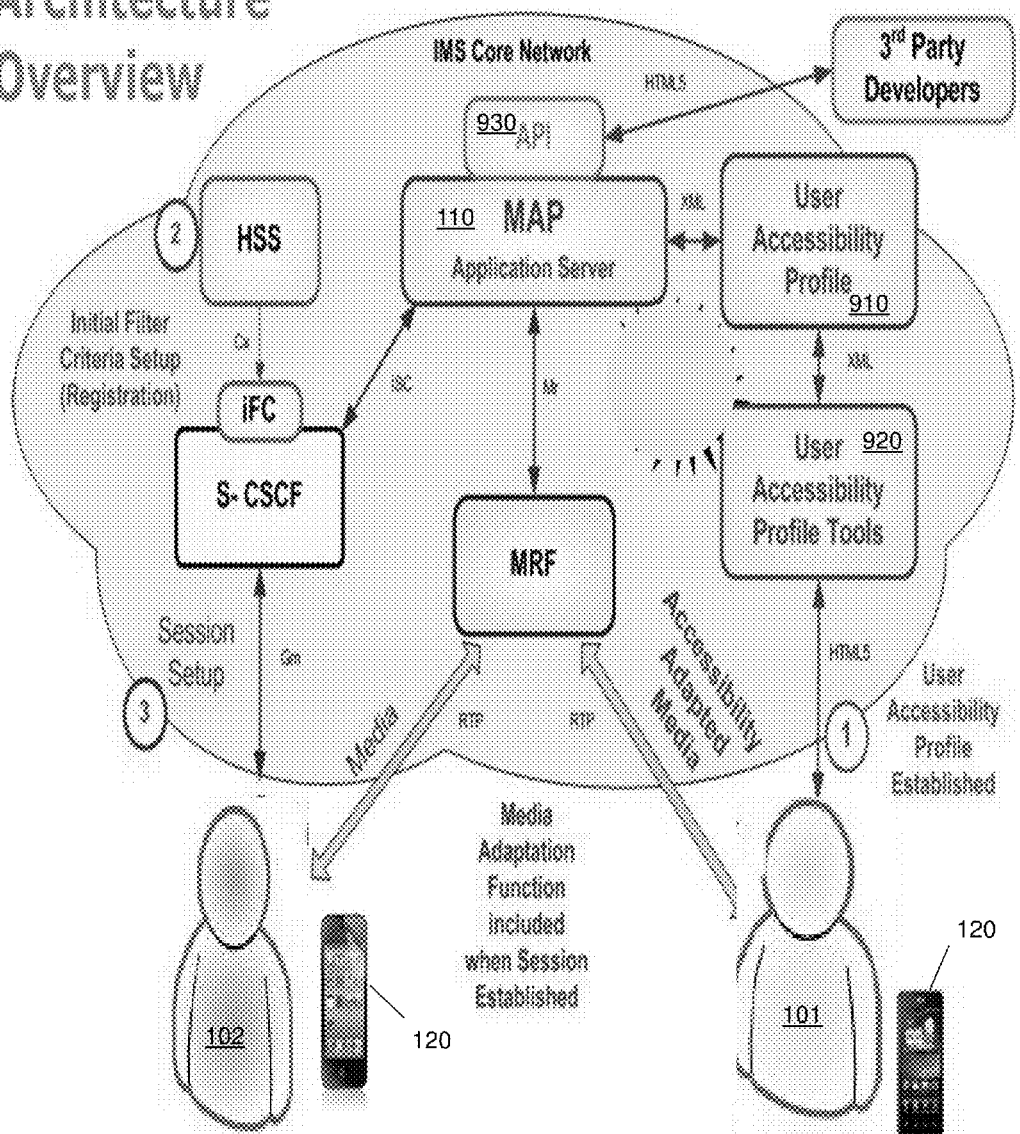

FIG. 9 depicts an illustrative embodiment of a communication system 900 for providing a communication session that can deliver voice, video and/or data, such as between users. In this embodiment, accessibility adaptation can be performed within an IMS core network by way of an application server operating as server 110. However, the exemplary embodiments also can include the server 110 operating in a network that is not an IMS core network. In one or more embodiments, the server 110 can be a separate device for providing multimedia accessibility adjustments. In one embodiment, system 900 enables IMS originating and terminating filter criteria to invoke the accessibility adjustment functionality of server 110 at session establishment.

Server 110 can be in communication with various components of the IMS network such as an Home Subscriber Server (HSS), Serving Call Session Control Function (S-CSCF), Media Resource Function (MRF) and so forth in order to facilitate establishing the communication session, monitoring the session and terminating the session. Server 110 can access profiles stored at storage devices 910 in the IMS network and can access tools 920 that can facilitate analysis of the profiles, as well as adjusting the multimedia content based on accessibility issues of the users.

In one or more embodiments, the system 900 can include an Application Programming Interface (API) 930 that is accessible by one or more remote devices operated by one or more third parties that are different from a service provider operating the system 900. In one or more embodiments, at least a portion of instructions for executing one or more adjustment techniques of the group of adjustment techniques can be received from the remote device (e.g., developed by third party developers that are independent of the service provider operating the IMS core network). System 900 can communicate various information amongst its components using various protocols such as HTML5, XML, RTP, and so forth.

Figure 10:
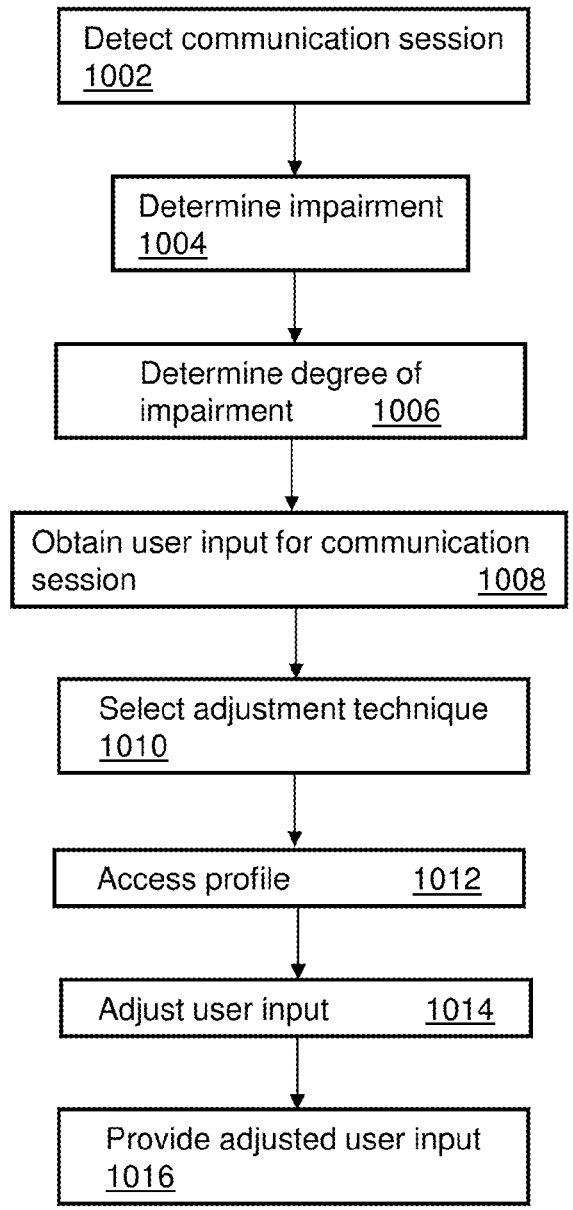
FIG. 10 depicts an illustrative embodiment of a method operating in portions of one or more of the systems described in FIGS. 1-9 and 11-12.

FIG. 10 illustrates a method 1000 that can be performed by one or more of the devices described in FIGS. 1-9 to provide accessibility adjustments during a communication session. Method 1000 can begin at 1002 where a communication session is detected, such as by an application server operating as server 110. At 1004, one or more impairments of one or both users can be detected or otherwise determined. The impairment can be identified based on various data, such as from a profile(s) associated with one or both users, user input entered at the time of the communication session, monitoring of previous communications associated with one or both of the users, user feedback from prior communication sessions and so forth. At 1006, a degree of the impairment can be determined such as from impairment information in the profile.

At 1008, user input can be captured during the communication session. The user input can be user speech, sign language images of the user, or other content (e.g., text, graphics, music and so forth). At 1010, an adjustment technique can be selected for adjusting the user input. In one embodiment, the adjustment technique can be selected from among a group of adjustment techniques. In one embodiment, the selection can be according to the degree of the impairment. In one embodiment, instructions can be stored for executing the group of adjustment techniques for modifying the user input, where the group of adjustment techniques includes amplifying selective frequencies for a first degree of impairment and translating the user input into sign language images for a second degree of impairment, and where the second degree of impairment is more severe than the first degree of impairment.

At 1012, an impairment profile can be accessed for the user(s) for whom the impairment was detected. At 1014, the user input can be adjusted according to the selected adjustment technique and the impairment profile to generate adjusted user input. At 1016, the adjusted user input can be provided to the end user device during the communication session. The providing of the adjusted user input can be in place of the original user input (e.g., replacing original user speech with modified user speech in which selected frequencies have been modified). In one or more embodiments, the adjusted user input is being provided as part of the communication session in real-time or near real time or otherwise without a user-noticeable delay.

Figure 11:
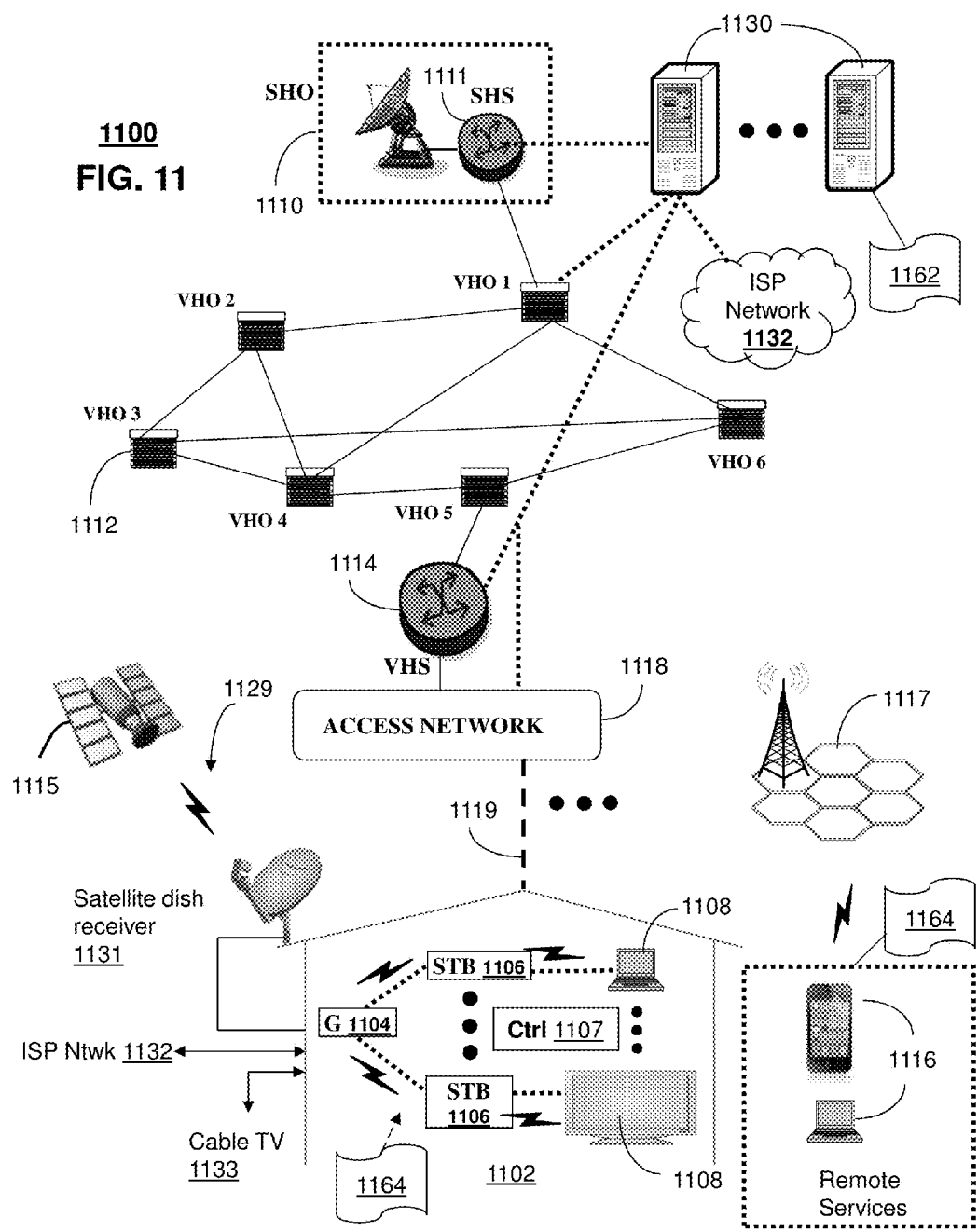
FIGS. 11-12 depict illustrative embodiments of systems for providing one or more accessibility adjustments such as during a communication session.

FIG. 11 depicts an illustrative embodiment of a communication system 1100 for delivering media content and providing communication sessions with accessibility adjustments. The communication system 1100 can represent an Internet Protocol Television (IPTV) media system. Communication system 1100 can be overlaid or operably coupled with systems 100-900 as another representative embodiment of communication system 1100. In one or more embodiments, system 1100 enables determining a first impairment associated with a first user of a first end user device and receiving user input captured at a second end user device during a communication session between the first and second end user devices. System 1100 enables storing instructions for executing a group of adjustment techniques for modifying the user input, where the group of adjustment techniques includes amplifying selective frequencies and translating the user input into sign language images. System 1100 enables selecting an adjustment technique from among the group of adjustment techniques, adjusting the user input according to the adjustment technique to generate adjusted user input, and providing the adjusted user input to the first end user device during the communication session. Various components of system 1100 will be described herein that can perform all or a portion of the accessibility adjustments of the exemplary embodiments, including the steps of method 1000.

The IPTV media system can include a super head-end office (SHO) 1110 with at least one super headend office server (SHS) 1111 which receives media content from satellite and/or terrestrial communication systems. In the present context, media content can represent, for example, audio content, moving image content such as 2D or 3D videos, video games, virtual reality content, still image content, and combinations thereof. The SHS server 1111 can forward packets associated with the media content to one or more video head-end servers (VHS) 1114 via a network of video head-end offices (VHO) 1112 according to a multicast communication protocol.

The VHS 1114 can distribute multimedia broadcast content via an access network 1118 to commercial and/or residential buildings 1102 housing a gateway 1104 (such as a residential or commercial gateway). The access network 1118 can represent a group of digital subscriber line access multiplexers (DSLAMs) located in a central office or a service area interface that provide broadband services over fiber optical links or copper twisted pairs 1119 to buildings 1102. The gateway 1104 can use communication technology to distribute broadcast signals to media processors 1106 such as Set-Top Boxes (STBs) which in turn present broadcast channels to media devices 1108 such as computers or television sets managed in some instances by a media controller 1107 (such as an infrared or RF remote controller).

The gateway 1104, the media processors 1106, and media devices 1108 can utilize tethered communication technologies (such as coaxial, powerline or phone line wiring) or can operate over a wireless access protocol such as Wireless Fidelity (WiFi), Bluetooth, Zigbee, or other present or next generation local or personal area wireless network technologies. By way of these interfaces, unicast communications can also be invoked between the media processors 1106 and subsystems of the IPTV media system for services such as video-on-demand (VoD), browsing an electronic programming guide (EPG), or other infrastructure services.

A satellite broadcast television system 1129 can be used in the media system of FIG. 11. The satellite broadcast television system can be overlaid, operably coupled with, or replace the IPTV system as another representative embodiment of communication system 1100. In this embodiment, signals transmitted by a satellite 1115 that include media content can be received by a satellite dish receiver 1131 coupled to the building 1102. Modulated signals received by the satellite dish receiver 1131 can be transferred to the media processors 1106 for demodulating, decoding, encoding, and/or distributing broadcast channels to the media devices 1108. The media processors 1106 can be equipped with a broadband port to an Internet Service Provider (ISP) network 1132 to enable interactive services such as VoD and EPG as described above.

In yet another embodiment, an analog or digital cable broadcast distribution system such as cable TV system 1133 can be overlaid, operably coupled with, or replace the IPTV system and/or the satellite TV system as another representative embodiment of communication system 1100. In this embodiment, the cable TV system 1133 can also provide Internet, telephony, and interactive media services.

The subject disclosure can apply to other present or next generation over-the-air and/or landline media content services system.

Some of the network elements of the IPTV media system can be coupled to one or more computing devices 1130, a portion of which can operate as a web server for providing web portal services over the ISP network 1132 to wireline media devices 1108 or wireless communication devices 1116.

Communication system 1100 can also provide for all or a portion of the computing devices 1130 to function as a multimedia accessibility platform (herein referred to as server 1130), including performing all or a portion of the functions of server 110 described with respect to systems 100-900. The server 1130 can use computing and communication technology to perform function 1162, which can include among other things, identifying one or more impairments associated with one or more users for a communication session, obtaining impairment information associated with the identified impairment(s), selecting an appropriate adjustment technique for captured or otherwise obtained content, adjusting the content (e.g., user speech, sign language images, text, graphics and so forth) based on the selected adjustment technique and the impairment information. The media processors 1106 and wireless communication devices 1116 can be provisioned with software functions 1164 to utilize the services of server 1130, such as providing impairment information, requesting an accessibility adjustment, performing an impairment test (e.g., an audio test to generate an audiogram), pre-processing of the captured content, processing some of the accessibility adjustment functions of method 1000 to create a distributed processing environment with the server 1130, and so forth.

Multiple forms of media services can be offered to media devices over landline technologies such as those described above. Additionally, media services can be offered to media devices by way of a wireless access base station 1117 operating according to common wireless access protocols such as Global System for Mobile or GSM, Code Division Multiple Access or CDMA, Time Division Multiple Access or TDMA, Universal Mobile Telecommunications or UMTS, World interoperability for Microwave or WiMAX, Software Defined Radio or SDR, Long Term Evolution or LTE, and so on. Other present and next generation wide area wireless access network technologies can be used in one or more embodiments of the subject disclosure.

Figure 12:
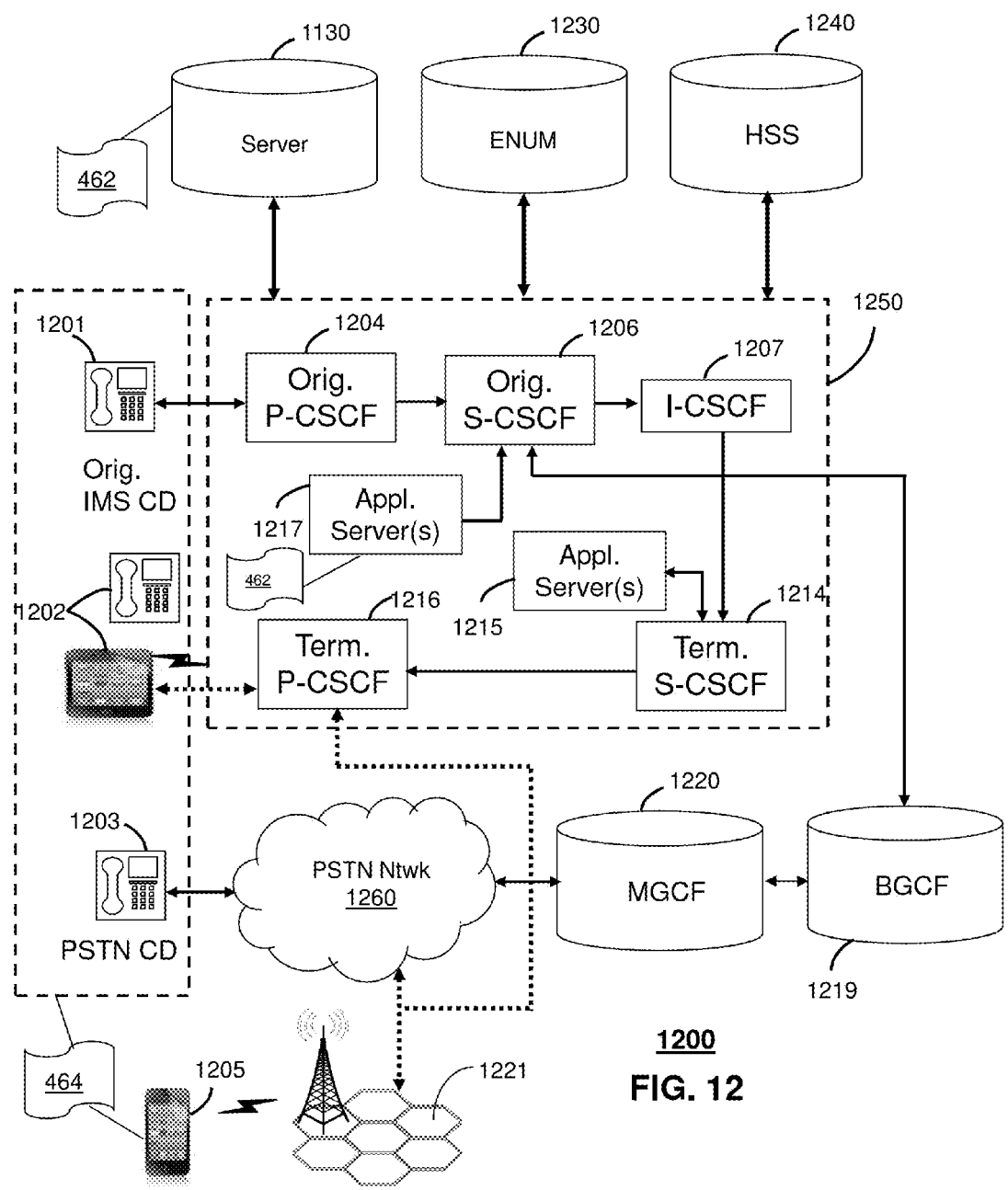

FIG. 12 depicts an illustrative embodiment of a communication system 1200 employing an IP Multimedia Subsystem (IMS) network architecture to facilitate the combined services of circuit-switched and packet-switched systems. Communication system 1200 can be overlaid or operably coupled with systems 100-900 and communication system 1100 as another representative embodiment of communication system 1200.

System 1200 enables end user devices to: provide impairment information, such as to an application server, receive adjusted user input as part of a communication session, and/or present the adjusted user input. The adjusted user input can be generated (e.g., by the application server) from a modification of user input captured at one of the end user devices during the communication session, where the modification is responsive to a detection of an impairment of a user. The adjusted user input can be based on an adjustment technique selected (e.g., by the application server) from among a group of adjustment techniques. Instructions for executing the group of adjustment techniques can be stored or otherwise be accessible (e.g., to the application server), where the group of adjustment techniques can include amplifying selective frequencies, converting speech to text, and/or translating user input into sign language images.

Communication system 1200 can comprise an HSS 1240, a tElephone NUmber Mapping (ENUM) server 1230, and other network elements of an IMS network 1250. The IMS network 1250 can establish communications between IMS-compliant communication devices (CDs) 1201, 1202, Public Switched Telephone Network (PSTN) CDs 1203, 1205, and combinations thereof by way of a Media Gateway Control Function (MGCF) 1220 coupled to a PSTN network 1260. The MGCF 1220 need not be used when a communication session involves IMS CD to IMS CD communications. A communication session involving at least one PSTN CD may utilize the MGCF 1220.

IMS CDs 1201, 1202 can register with the IMS network 1250 by contacting a Proxy Call Session Control Function (P-CSCF) which communicates with an interrogating CSCF (I-CSCF), which in turn, communicates with a S-CSCF to register the CDs with the HSS 1240. To initiate a communication session between CDs, an originating IMS CD 1201 can submit a Session Initiation Protocol (SIP INVITE) message to an originating P-CSCF 1204 which communicates with a corresponding originating S-CSCF 1206. The originating S-CSCF 1206 can submit the SIP INVITE message to one or more application servers (ASs) 1217 that can provide a variety of services to IMS subscribers.

For example, the application servers 1217 can be used to perform originating call feature treatment functions on the calling party number received by the originating S-CSCF 1206 in the SIP INVITE message. Originating treatment functions can include determining whether the calling party number has international calling services, call ID blocking, calling name blocking, 7-digit dialing, and/or is requesting special telephony features (e.g., *72 forward calls, *73 cancel call forwarding, *67 for caller ID blocking, and so on). Based on initial filter criteria (iFCs) in a subscriber profile associated with a CD, one or more application servers may be invoked to provide various call originating feature services.

Additionally, the originating S-CSCF 1206 can submit queries to the ENUM system 1230 to translate an E.164 telephone number in the SIP INVITE message to a SIP Uniform Resource Identifier (URI) if the terminating communication device is IMS-compliant. The SIP URI can be used by an Interrogating CSCF (I-CSCF) 1207 to submit a query to the HSS 1240 to identify a terminating S-CSCF 1214 associated with a terminating IMS CD such as reference 1202. Once identified, the I-CSCF 1207 can submit the SIP INVITE message to the terminating S-CSCF 1214. The terminating S-CSCF 1214 can then identify a terminating P-CSCF 1216 associated with the terminating CD 1202. The P-CSCF 1216 may then signal the CD 1202 to establish Voice over Internet Protocol (VoIP) communication services, thereby enabling the calling and called parties to engage in voice and/or data communications. Based on the iFCs in the subscriber profile, one or more application servers may be invoked to provide various call terminating feature services, such as call forwarding, do not disturb, music tones, simultaneous ringing, sequential ringing, etc.

In some instances the aforementioned communication process is symmetrical. Accordingly, the terms "originating" and "terminating" in FIG. 12 may be interchangeable. It is further noted that communication system 1200 can be adapted to support video conferencing. In addition, communication system 1200 can be adapted to provide the IMS CDs 1201, 1202 with the multimedia and Internet services of communication system 1100 of FIG. 11.

If the terminating communication device is instead a PSTN CD such as CD 1203 or CD 1205 (in instances where the cellular phone only supports circuit-switched voice communications), the ENUM system 1230 can respond with an unsuccessful address resolution which can cause the originating S-CSCF 1206 to forward the call to the MGCF 1220 via a Breakout Gateway Control Function (BGCF) 1219. The MGCF 1220 can then initiate the call to the terminating PSTN CD over the PSTN network 1260 to enable the calling and called parties to engage in voice and/or data communications.

It is further appreciated that the CDs of FIG. 12 can operate as wireline or wireless devices. For example, the CDs of FIG. 12 can be communicatively coupled to a cellular base station 1221, a femtocell, a WiFi router, a Digital Enhanced Cordless Telecommunications (DECT) base unit, or another suitable wireless access unit to establish communications with the IMS network 1250 of FIG. 12. The cellular access base station 1221 can operate according to common wireless access protocols such as GSM, CDMA, TDMA, UMTS, WiMax, SDR, LTE, and so on. Other present and next generation wireless network technologies can be used by one or more embodiments of the subject disclosure. Accordingly, multiple wireline and wireless communication technologies can be used by the CDs of FIG. 12.

Cellular phones supporting LTE can support packet-switched voice and packet-switched data communications and thus may operate as IMS-compliant mobile devices. In this embodiment, the cellular base station 1221 may communicate directly with the IMS network 1250 as shown by the arrow connecting the cellular base station 1221 and the P-CSCF 1216.

It is further understood that alternative forms of a CSCF can operate in a device, system, component, or other form of centralized or distributed hardware and/or software. Indeed, a respective CSCF may be embodied as a respective CSCF system having one or more computers or servers, either centralized or distributed, where each computer or server may be configured to perform or provide, in whole or in part, any method, step, or functionality described herein in accordance with a respective CSCF. Likewise, other functions, servers and computers described herein, including but not limited to, the HSS, the ENUM server, the BGCF, and the MGCF, can be embodied in a respective system having one or more computers or servers, either centralized or distributed, where each computer or server may be configured to perform or provide, in whole or in part, any method, step, or functionality described herein in accordance with a respective function, server, or computer.

In one or more embodiments, the server 1130 of FIG. 11 can be operably coupled to the communication system 1200 for purposes similar to those described above. Server 1130 can perform functions 462 and thereby provide accessibility adjustment services to the CDs 1201, 1202, 1203 and 1205 of FIG. 12. CDs 1201, 1202, 1203 and 1205, which can be adapted with software to perform functions 464 to utilize the services of the server 1130 and/or the application server 1217. In other embodiments, server 1130 can be an integral part of the application server(s) 1217 performing functions 462. In one embodiment, server 1130 and application server 1217 can perform a distributed environment for performing the accessibility adjustments.

For illustration purposes only, the terms S-CSCF, P-CSCF, I-CSCF, and so on, can be server devices, but may be referred to in the subject disclosure without the word "server." It is also understood that any form of a CSCF server can operate in a device, system, component, or other form of centralized or distributed hardware and software. It is further noted that these terms and other terms such as DIAMETER commands are terms can include features, methodologies, and/or fields that may be described in whole or in part by standards bodies such as $3^{rd}$ Generation Partnership Project (3GPP). It is further noted that some or all embodiments of the subject disclosure may in whole or in part modify, supplement, or otherwise supersede final or proposed standards published and promulgated by 3GPP.

Figure 13:
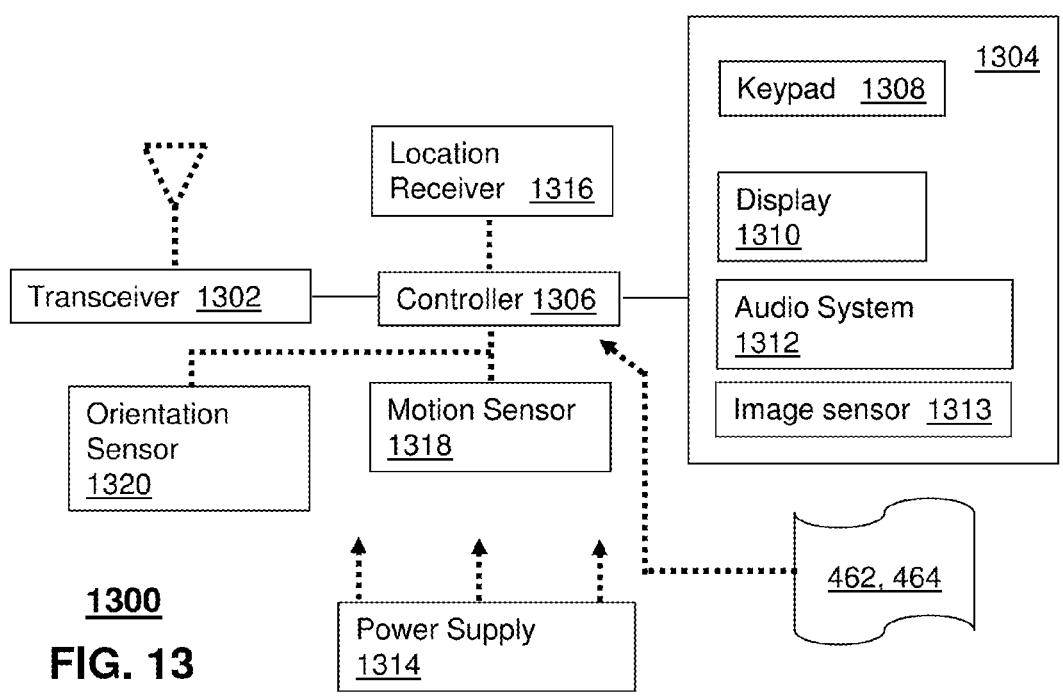
FIG. 13 depicts an illustrative embodiment of a communication device that can perform or otherwise facilitate accessibility adjustments such as during a communication session.

FIG. 13 depicts an illustrative embodiment of a communication device 1300. Communication device 1300 can serve in whole or in part as an illustrative embodiment of the devices depicted in FIGS. 1-9 and 11-12, including server 110, server 1130, application server 1217, end user devices 120, and so forth. As an example, device 1300 can provide impairment information such as to application server 1217 of FIG. 12. Device 1300 can receive adjusted user input from the server 1217 during a communication session between the device and a second end user device, wherein the adjusted user input is generated from a modification of user input captured at the second end user device during the communication session. The modification can be responsive to a detection of a first impairment of a first user of the device 1300 and can be based on an adjustment technique selected by the server 1217 from among a group of adjustment techniques. In one embodiment, instructions for executing the group of adjustment techniques can be accessible to the server 1217, and the group of adjustment techniques can include amplifying selective frequencies and translating the user input into sign language images. The device 1300 can present the adjusted user input at the first end user device. In one embodiment, the device 1300 can capture other user input at a user interface, and can provide the other user input to the server 1217 to enable the server to generate adjusted other user input responsive to a detection of a second impairment of a second user of the second end user device and based on another adjustment technique selected by the server 1217 from among the group of adjustment techniques. The server 1217 can provide the adjusted other user input to the second end user device for presentation.

To enable these features, communication device 1300 can comprise a wireline and/or wireless transceiver 1302 (herein transceiver 1302), a user interface (UI) 1304, a power supply 1314, a location receiver 1316, a motion sensor 1318, an orientation sensor 1320, and a controller 1306 for managing operations thereof. The transceiver 1302 can support short-range or long-range wireless access technologies such as Bluetooth, ZigBee, WiFi, DECT, or cellular communication technologies, just to mention a few. Cellular technologies can include, for example, CDMA-1x, UMTS/HSDPA, GSM/GPRS, TDMA/EDGE, EV/DO, WiMAX, SDR, LTE, as well as other next generation wireless communication technologies as they arise. The transceiver 1302 can also be adapted to support circuit-switched wireline access technologies (such as PSTN), packet-switched wireline access technologies (such as TCP/IP, VoIP, etc.), and combinations thereof.

The UI 1304 can include a depressible or touch-sensitive keypad 1308 with a navigation mechanism such as a roller ball, a joystick, a mouse, or a navigation disk for manipulating operations of the communication device 1300. The keypad 1308 can be an integral part of a housing assembly of the communication device 1300 or an independent device operably coupled thereto by a tethered wireline interface (such as a USB cable) or a wireless interface supporting for example Bluetooth. The keypad 1308 can represent a numeric keypad commonly used by phones, and/or a QWERTY keypad with alphanumeric keys. The UI 1304 can further include a display 1310 such as monochrome or color LCD (Liquid Crystal Display), OLED (Organic Light Emitting Diode) or other suitable display technology for conveying images to an end user of the communication device 1300. In an embodiment where the display 1310 is touch-sensitive, a portion or all of the keypad 1308 can be presented by way of the display 1310 with navigation features.

The display 1310 can use touch screen technology to also serve as a user interface for detecting user input. As a touch screen display, the communication device 1300 can be adapted to present a user interface with graphical user interface (GUI) elements that can be selected by a user with a touch of a finger. The touch screen display 1310 can be equipped with capacitive, resistive or other forms of sensing technology to detect how much surface area of a user's finger has been placed on a portion of the touch screen display. This sensing information can be used to control the manipulation of the GUI elements or other functions of the user interface. The display 1310 can be an integral part of the housing assembly of the communication device 1300 or an independent device communicatively coupled thereto by a tethered wireline interface (such as a cable) or a wireless interface.

The UI 1304 can also include an audio system 1312 that utilizes audio technology for conveying low volume audio (such as audio heard in proximity of a human ear) and high volume audio (such as speakerphone for hands free operation). The audio system 1312 can further include a microphone for receiving audible signals of an end user. The audio system 1312 can also be used for voice recognition applications. The UI 1304 can further include an image sensor 1313 such as a charged coupled device (CCD) camera for capturing still or moving images.

The power supply 1314 can utilize common power management technologies such as replaceable and rechargeable batteries, supply regulation technologies, and/or charging system technologies for supplying energy to the components of the communication device 1300 to facilitate long-range or short-range portable applications. Alternatively, or in combination, the charging system can utilize external power sources such as DC power supplied over a physical interface such as a USB port or other suitable tethering technologies.

The location receiver 1316 can utilize location technology such as a global positioning system (GPS) receiver capable of assisted GPS for identifying a location of the communication device 1300 based on signals generated by a constellation of GPS satellites, which can be used for facilitating location services such as navigation. The motion sensor 1318 can utilize motion sensing technology such as an accelerometer, a gyroscope, or other suitable motion sensing technology to detect motion of the communication device 1300 in three-dimensional space. The orientation sensor 1320 can utilize orientation sensing technology such as a magnetometer to detect the orientation of the communication device 1300 (north, south, west, and east, as well as combined orientations in degrees, minutes, or other suitable orientation metrics).

The communication device 1300 can use the transceiver 1302 to also determine a proximity to a cellular, WiFi, Bluetooth, or other wireless access points by sensing techniques such as utilizing a received signal strength indicator (RSSI) and/or signal time of arrival (TOA) or time of flight (TOF) measurements. The controller 1306 can utilize computing technologies such as a microprocessor, a digital signal processor (DSP), programmable gate arrays, application specific integrated circuits, and/or a video processor with associated storage memory such as Flash, ROM, RAM, SRAM, DRAM or other storage technologies for executing computer instructions, controlling, and processing data supplied by the aforementioned components of the communication device 1300.

Other components not shown in FIG. 13 can be used in one or more embodiments of the subject disclosure. For instance, the communication device 1300 can include a reset button (not shown). The reset button can be used to reset the controller 1306 of the communication device 1300. In yet another embodiment, the communication device 1300 can also include a factory default setting button positioned, for example, below a small hole in a housing assembly of the communication device 1300 to force the communication device 1300 to re-establish factory settings. In this embodiment, a user can use a protruding object such as a pen or paper clip tip to reach into the hole and depress the default setting button. The communication device 1300 can also include a slot for adding or removing an identity module such as a Subscriber Identity Module (SIM) card. SIM cards can be used for identifying subscriber services, executing programs, storing subscriber data, and so forth.

The communication device 1300 as described herein can operate with more or less of the circuit components shown in FIG. 13. These variant embodiments can be used in one or more embodiments of the subject disclosure.

The communication device 1300 can be adapted to perform the functions of the servers 110, 1130, 1217 of FIGS. 1-9 and 11-12, the media processor 1106, the media devices 1108, or the portable communication devices 1116 of FIG. 11, as well as the IMS CDs 1201-1202 and PSTN CDs 1203-1205 of FIG. 12. It will be appreciated that the communication device 1300 can also represent other devices that can operate in communication systems 100-900 and 1100-1200 of FIGS. 1-9 and 11-12 such as a gaming console and a media player.

The communication device 1300 shown in FIG. 13 or portions thereof can serve as a representation of one or more of the devices of systems 100-900 and 1100-1200. In addition, the controller 1306 can be adapted in various embodiments to perform the functions 462 and 464 in order to facilitate accessibility adjustments.

Upon reviewing the aforementioned embodiments, it would be evident to an artisan with ordinary skill in the art that said embodiments can be modified, reduced, or enhanced without departing from the scope of the claims described below. For example, the accessibility adjustments can be performed for more than two users involved in a communication session. As an example, a conference call amongst three or more users at three or more different end user devices can result in various user input adjustments being made and delivered to the respective user based on an impairment of that user. For instance, the first user may desire selective frequency amplification of user speech, the second user may desire a speech-to-text conversion, and the third user may desire a speech-to-sign language conversion. In this example, the server 110 (or other device performing the accessibility adjustment) would perform multiple adjustments on the same user input to satisfy the desires of the recipients.

In another embodiment, there may be multiple users utilizing a single first end user device that is in a communication with a second end user device. In this example, the server 110 (or other device performing the accessibility adjustment) would determine the adjustments to be made which would satisfy the desires of the multiple users at the single device. For example, if one of the first users has a mild hearing impairment and another of the users has a severe hearing impairment then the server may select a speech-totext conversion of the user speech. In other embodiments, multiple conversions can be performed to satisfy both impairments, such as delivering both adapted user speech (e.g., amplifying selected frequencies based on an audiogram) and sign language images to the single first end user device.

In one or more embodiments, the conversion of the user input (e.g., user speech) may not be verbatim. For instance, words or phrases can be changed based on a number of factors, such as education level of the recipient. In another embodiment, certain words may be changed to account for other impairments, such as trying to avoid certain words based on detecting a recipient user that has dyslexia.

In one or more embodiments, the user input can be content that is obtained from another source rather than captured at the device. For example, a first user may download and transmit a color image to a second user where colors can be modified in color image by server 110 to account for a detected color blindness of the second user.

In one or more embodiments, cognitive impairments can be addressed. As an example, a user with limited reading ability (e.g., in a developing country) may rent or otherwise temporarily obtain a cell phone. The user may speak his or her name, which is recognized and authenticated. The user may be provided with an icon based interface that minimizes reading dependency. The user's personal Enhanced Address Book (EAB) can be downloaded from server 110 to the end user device. The user can see images of friends, their communication capabilities, and/or social presence information of the user's contacts (e.g., RCS functionality). The user can tap on a video icon by a friend's image, and a video call can be established. In this embodiment, iconography can be implemented by the server 110 to facilitate the communication session based on a detected or determined cognitive impairment of the user. Other accessibility adjustments can also be performed including language translations.

In one or more embodiments, end user devices can be automatically provisioned (e.g., at the time of purchase of the device) with information and software to make use of the accessibility adjustment functionality of server 110. Other embodiments can be used in the subject disclosure.

It should be understood that devices described in the exemplary embodiments can be in communication with each other via various wireless and/or wired methodologies. The methodologies can be links that are described as coupled, connected and so forth, which can include unidirectional and/or bidirectional communication over wireless paths and/or wired paths that utilize one or more of various protocols or methodologies, where the coupling and/or connection can be direct (e.g., no intervening processing device) and/or indirect (e.g., an intermediary processing device such as a router).

Figure 14:
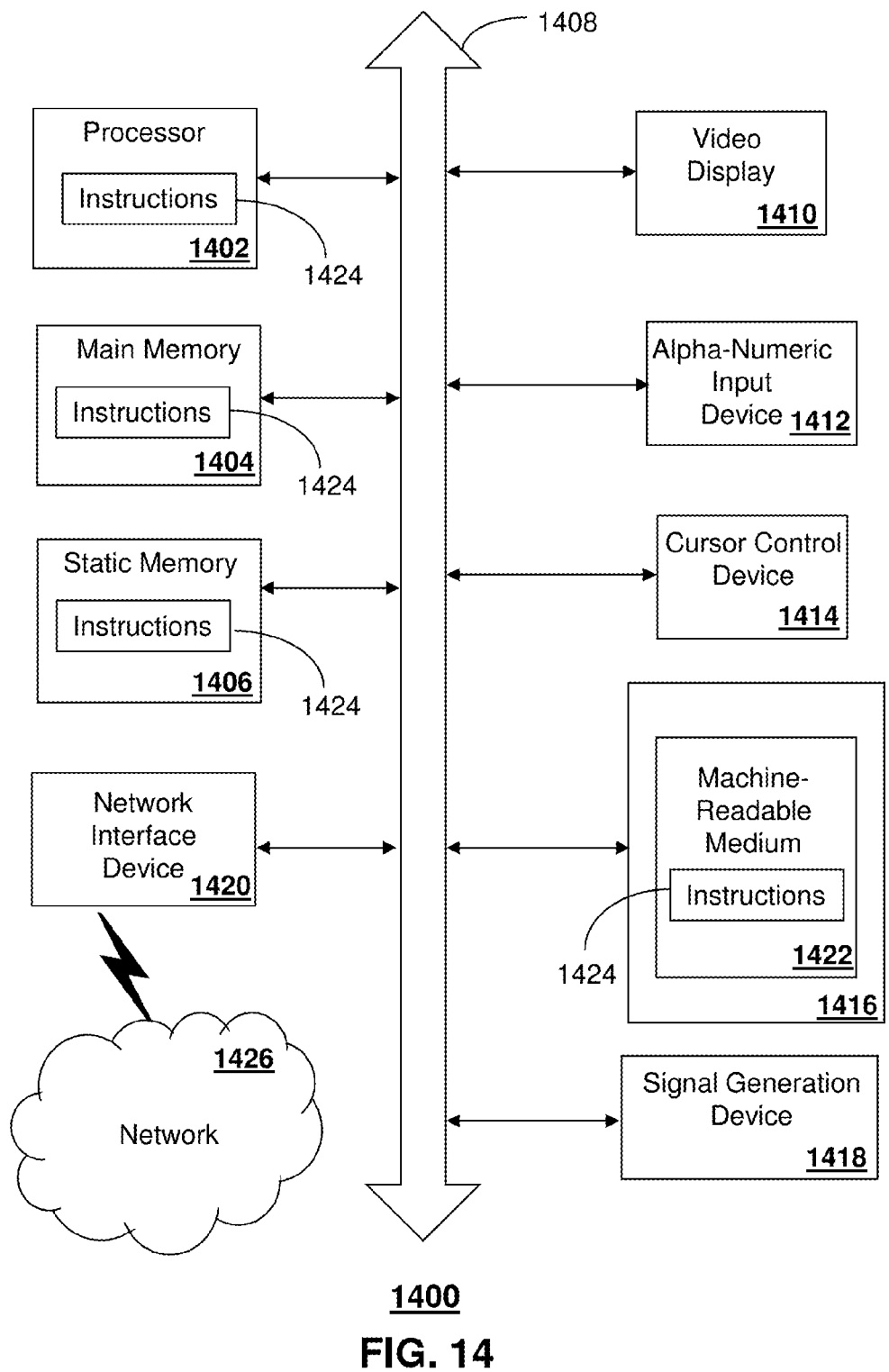
FIG. 14 is a diagrammatic representation of a machine in the form of a computer system within which a set of instructions, when executed, may cause the machine to perform any one or more of the methods described herein.

FIG. 14 depicts an exemplary diagrammatic representation of a machine in the form of a computer system 1400 within which a set of instructions, when executed, may cause the machine to perform any one or more of the methods describe above. One or more instances of the machine can operate, for example, as the server 110, 1130, 1217 and other devices of FIGS. 1-9 and 10-13 in order to perform accessibility adjustments. In some embodiments, the machine may be connected (e.g., using a network 1426) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 1400 may include a processor (or controller) 1402 (e.g., a central processing unit (CPU), a graphics processing unit (GPU, or both), a main memory 1404 and a static memory 1406, which communicate with each other via a bus 1408. The computer system 1400 may further include a display unit 1410 (e.g., a liquid crystal display (LCD), a flat panel, or a solid state display. The computer system 1400 may include an input device 1412 (e.g., a keyboard), a cursor control device 1414 (e.g., a mouse), a disk drive unit 1416, a signal generation device 1418 (e.g., a speaker or remote control) and a network interface device 1420. In distributed environments, the embodiments described in the subject disclosure can be adapted to utilize multiple display units 1410 controlled by two or more computer systems 1400. In this configuration, presentations described by the subject disclosure may in part be shown in a first of the display units 1410, while the remaining portion is presented in a second of the display units 1410.

The disk drive unit 1416 may include a tangible computer-readable storage medium 1422 on which is stored one or more sets of instructions (e.g., software 1424) embodying any one or more of the methods or functions described herein, including those methods illustrated above. The instructions 1424 may also reside, completely or at least partially, within the main memory 1404, the static memory 1406, and/or within the processor 1402 during execution thereof by the computer system 1400. The main memory 1404 and the processor 1402 also may constitute tangible computer-readable storage media.

Dedicated hardware implementations including, but not limited to, application specific integrated circuits, programmable logic arrays and other hardware devices that can likewise be constructed to implement the methods described herein. Application specific integrated circuits and programmable logic array can use downloadable instructions for executing state machines and/or circuit configurations to implement embodiments of the subject disclosure. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the operations or methods described herein are intended for operation as software programs or instructions running on or executed by a computer processor or other computing device, and which may include other forms of instructions manifested as a state machine implemented with logic components in an application specific integrated circuit or field programmable array. Furthermore, software implementations (e.g., software programs, instructions, etc.) can include, but not limited to, distributed processing or component/object distributed processing, parallel processing, or virtual machine processing can also be constructed to implement the methods described herein. It is further noted that a computing device such as a processor, a controller, a state machine or other suitable device for executing instructions to perform operations or methods may perform such operations directly or indirectly by way of one or more intermediate devices directed by the computing device.

While the tangible computer-readable storage medium 1422 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure. The term "non-transitory" as in a non-transitory computer-readable storage includes without limitation memories, drives, devices and anything tangible but not a signal per se.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID), short-range communications (e.g., Bluetooth, WiFi, Zigbee), and long-range communications (e.g., WiMAX, GSM, CDMA, LTE) can be used by computer system 1400.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, can be used in the subject disclosure. In one or more embodiments, features that are positively recited can also be excluded from the embodiment with or without replacement by another component or step. The steps or functions described with respect to the exemplary processes or methods can be performed in any order. The steps or functions described with respect to the exemplary processes or methods can be performed alone or in combination with other steps or functions (from other embodiments or from other steps that have not been described). Less than all of the steps or functions described with respect to the exemplary processes or methods can also be performed in one or more of the exemplary embodiments. Further, the use of numerical terms to describe a device, component, step or function, such as first, second, third, and so forth, is not intended to describe an order or function unless expressly stated so. The use of the terms first, second, third and so forth, is generally to distinguish between devices, components, steps or functions unless expressly stated otherwise. Additionally, one or more devices or components described with respect to the exemplary embodiments can facilitate one or more steps or functions, where the facilitating (e.g., facilitating access or facilitating establishing a connection) can include less than all of the steps needed to perform the function or can include all of the steps of the function.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A method, comprising:
    storing, by a system including a processor, instructions for executing adjustment techniques for modifying user input, wherein first adjustment techniques include amplifying selective frequencies for a first degree of impairment and translating user input into first sign language images for a second degree of impairment, wherein second adjustment techniques include translating user input from sign language images into synthesized audio speech, wherein the second degree of impairment is more severe than the first degree of impairment;
    detecting, by the system, a communication session between a first end user device and a second end user device;
    determining, by the system, a first impairment associated with a first user of the first end user device and a second impairment associated with a second user of the second end user device;

determining, by the system, a degree of impairment for the second impairment;

receiving, by the system, a first user input captured at the first end user device and a second user input captured at the second end user device during the communication session;

selecting, by the system, a selected adjustment technique from among the first adjustment techniques according to the degree of impairment for the second impairment;

accessing, by the system, an impairment profile for the first user;

adjusting, by the system, the second user input according to the impairment profile to generate adjusted second user output;

adjusting, by the system, the first user input according to the impairment profile and then applying the selected adjustment technique to generate adjusted synthesized audio speech as adjusted first user output; and providing, by the system, the adjusted first user output to the second end user device and the adjusted second user output to the first end user device during the communication session.

2. The method of claim 1, comprising:
obtaining user preferences for the first user from the impairment profile; and
generating the first sign language images to include an avatar for presenting sign language representative of the user input, wherein physical characteristics of the avatar are generated based on the user preferences.

3. The method of claim 2, comprising:
accessing a sign language library associated with the first user; and
generating the first sign language images according to the sign language library, wherein the first adjustment techniques further includes translating the second user input into text.

4. The method of claim 1, wherein the impairment profile includes an audiogram for the first user, and wherein the selective frequencies that are amplified are selected based on the audiogram.

5. The method of claim 4, comprising:
providing a hearing test at a communication device of the first user prior to the communication session; and
generating the audiogram based on the hearing test.

6. The method of claim 4, comprising obtaining the audiogram from a remote source operated by a third party that is different from a service provider operating the system.

7. The method of claim 1, wherein the first adjustment techniques includes one of modifying one of a size, color or font of text or replacing a word with another word based on a determined cognitive impairment.

8. The method of claim 1, comprising:
determining, by the system, a third impairment associated with the second user of the second end user device;
determining, by the system, a third degree of impairment for the third impairment;
selecting, by the system, a second selected adjustment technique from the second adjustment techniques according to the third degree of impairment for the third impairment; and
accessing, by the system, a second impairment profile for the second user,
wherein the first user input is adjusted according to the second selected adjustment technique and the second impairment profile to generate the adjusted first user output.

9. The method of claim 1, wherein the impairment profile includes vision information for the first user, wherein the first adjustment techniques include modifying graphics generated at the first end user device according to the vision information and further comprising:
obtaining the vision information for the first user by one of a vision test at a communication device of the first user prior to the communication session or receiving the vision information from a remote source operated by a third party that is different from a service provider operating the system.

10. The method of claim 1, wherein the second user input and the adjusted second user output are both provided to the first end user device during the communication session.

11. The method of claim 1, wherein the system comprises an application programming interface accessible by a remote device that is operated by a third party that is different from a service provider operating the system, and wherein at least a portion of the instructions for executing the first adjustment techniques and the second adjustment techniques are received from the remote device.

12. The method of claim 1, wherein the system is an application server of an IP multimedia subsystem network that facilitates combined services of circuit-switched and packet-switched systems, and wherein the system is in communication with a serving call session control function and a media resource function of the IP multimedia subsystem network.

13. A system, comprising:
a memory to store executable instructions; and
a processor coupled with the memory, wherein the processor, responsive to executing the executable instructions, performs operations comprising:
storing instructions for executing first adjustment techniques for modifying first user input and second adjustment techniques for modifying user input, wherein the first adjustment techniques include amplifying selective frequencies and translating the user input into first sign language images, and wherein the second adjustment techniques include translating the user input from sign language images into first synthesized audio speech;
determining a first impairment associated with a deaf first user of a first end user device;
receiving a first user input captured at the first end user device and a second user input captured at a second end user device during a communication session between the first end user device and the second end user device;
selecting a first selected adjustment technique from the first adjustment techniques and a second selected adjustment technique from the second adjustment techniques according to the first impairment;
determining a second impairment associated with a hearing impaired second user of the second end user device;
selecting amplifying selective frequencies as a third selected adjustment technique from the first adjustment techniques according to the second impairment;
adjusting the second user input according to the first selected adjustment technique to generate adjusted second user output;
generating first synthesized audio speech from the first user input according to the second selected adjustment technique and the third selected adjustment technique as adjusted first user output; and providing the adjusted first user output to the second end user device and the adjusted second user output to the first end user device during the communication session.

14. The system of claim 13, wherein the operations further comprise:
determining a degree of impairment for the first impairment, wherein the selecting of the first selected adjustment technique from the first adjustment techniques is according to the degree of impairment for the first impairment; and
accessing an impairment profile for the deaf first user, wherein the adjusting of the second user input to generate the adjusted second user output is according to the impairment profile,
wherein the amplifying of the selective frequencies is utilized for a first degree of impairment, wherein the translating of the second user input into first sign language images is utilized for a second degree of impairment, and wherein the second degree of impairment is more severe than the first degree of impairment.

15. The system of claim 13, comprising an application programming interface accessible by a remote device that is operated by a third party that is different from a service provider operating the system, wherein at least a portion of the instructions for executing the first adjustment techniques and the second adjustment techniques are received from the remote device.

16. The system of claim 13, wherein the processor comprises an application server of an IP multimedia subsystem network that facilitates combined services of circuit-switched and packet-switched systems, and wherein the processor is in communication with a serving call session control function and a media resource function of the IP multimedia subsystem network.

17. The system of claim 13, wherein the operations further comprise:
accessing an impairment profile for the deaf first user, wherein the adjusting of the second user input to generate the adjusted second user output is according to the impairment profile, wherein the impairment profile includes vision information for the deaf first user, and wherein the first adjustment techniques include modifying graphics generated at the first end user device according to the vision information; and
obtaining the vision information for the deaf first user by one of a vision test at a communication device of the deaf first user prior to the communication session or receiving the vision information from a remote source operated by a third party that is different from a service provider operating the system.

18. A non-transitory computer-readable storage device comprising computer instructions which, responsive to being executed by a processor of a first end user device, cause the processor to perform operations comprising:
providing impairment information to a system that includes an application server;
receiving adjusted second user output from the system during a communication session between the first end user device and a second end user device, wherein the adjusted second user output is generated from a modification of a second user input captured at the second end user device during the communication session, wherein the modification is responsive to a detection of a first impairment of a first user of the first end user device and a second impairment of a second user of the second end user device and is based on selected adjustment techniques selected by the system from among second adjustment techniques and first adjustment techniques applied consecutively, wherein instructions for executing the first and second adjustment techniques are accessible to the system, wherein the first adjustment techniques include amplifying selective frequencies and translating the second user input into first sign language images, wherein the second adjustment techniques include translating user input from sign language images into synthesized audio speech, wherein first user input is adjusted by the system to generate adjusted synthesized audio speech from second sign language images from the first end user device, wherein the adjusted synthesized audio speech is delivered to the second end user device for presentation at the second end user device; and
presenting the adjusted second user output at the first end user device.

19. The non-transitory computer-readable storage device of claim 18, wherein the operations further comprise:
capturing the first user input at the first end user device; and
providing the first user input to the system to enable the system to generate adjusted first user output responsive to the detection of the second impairment of the second user of the second end user device and based on a second selected adjustment technique that is selected by the system from first adjustment techniques.

* * * * *